United States Patent
Muller et al.

(10) Patent No.: US 11,680,938 B2
(45) Date of Patent: Jun. 20, 2023

(54) SYSTEM AND METHOD OF CHARACTERIZING CRUDE OIL AND ITS DERIVATIVES BY COMBINING TOTAL SULFUR DETERMINATION AND FT-ICR MASS SPECTROMETRY

(71) Applicant: Saudi Arabian Oil Company, Dhahran (SA)

(72) Inventors: Hendrik Muller, Dhahran (SA); Nadrah Abdullah Alawani, Dhahran (SA); Ibrahim E. Al-Naimi, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 1035 days.

(21) Appl. No.: 16/446,871

(22) Filed: Jun. 20, 2019

(65) Prior Publication Data
US 2020/0400645 A1 Dec. 24, 2020

(51) Int. Cl.
G01N 33/28 (2006.01)
G01N 33/24 (2006.01)
H01J 49/00 (2006.01)
H01J 49/38 (2006.01)
H01J 49/40 (2006.01)

(52) U.S. Cl.
CPC ....... G01N 33/2823 (2013.01); G01N 33/241 (2013.01); G01N 33/287 (2013.01); H01J 49/004 (2013.01); H01J 49/38 (2013.01); H01J 49/40 (2013.01)

(58) Field of Classification Search
CPC ....... H01J 49/38; H01J 49/40; G01N 33/2823
See application file for complete search history.

(56) References Cited

U.S. PATENT DOCUMENTS

| 5,699,269 A | 12/1997 | Ashe et al. |
| 6,662,116 B2 | 12/2003 | Brown |
| 8,084,264 B2 | 12/2011 | Marshall et al. |
| 8,332,162 B2 | 12/2012 | Abahri |

(Continued)

FOREIGN PATENT DOCUMENTS

| WO | 2011141826 A1 | 11/2011 |
| WO | 2012083095 A2 | 6/2012 |

(Continued)

OTHER PUBLICATIONS

Yur E. Corilo et al., "Calculation of the Total Sulfur Content in Crude Oils by Positive-Ion Atmospheric Pressure Photoionization Fourier Transform Ion Cyclotron Resonance Mass Spectrometry," Energy Fuels, 2016, 30 (5), pp. 3962-3966.

(Continued)

*Primary Examiner* — Joseph L Williams
(74) *Attorney, Agent, or Firm* — Leason Ellis LLP

(57) ABSTRACT

A method and system to determine mass fraction of aromatic hydrocarbons, sulfur-multi-sulfur, sulfur-nitrogen, multi-sulfur-multi-nitrogen, and nitrogen containing aromatic compound classes present within a petroleum sample. The invention uses total sulfur determination, total nitrogen determination, and elemental formulas determination, with the latter determined through time-of-flight mass spectrometric analysis with atmospheric pressure photo ionization and Fourier-transform ion-cyclotron resonance mass spectrometric analysis with atmospheric pressure photo ionization.

13 Claims, 7 Drawing Sheets

(56) References Cited

U.S. PATENT DOCUMENTS

| | | |
|---|---|---|
| 8,530,834 B2 | 9/2013 | Marshall et al. |
| 9,111,735 B1 | 8/2015 | Nikolaev et al. |
| 9,417,220 B2 | 8/2016 | Wang et al. |
| 9,418,828 B2 | 8/2016 | Mennito et al. |
| 9,490,109 B2 | 11/2016 | Qian et al. |
| 9,625,439 B2 | 4/2017 | Saeger et al. |
| 9,665,693 B2 | 5/2017 | Saeger et al. |
| 9,846,147 B2 | 12/2017 | Kumar et al. |
| 10,068,761 B2 | 9/2018 | Wildgoose |
| 2013/0161502 A1 | 6/2013 | Pomerantz et al. |
| 2013/0206980 A1 | 8/2013 | Mennito et al. |
| 2015/0107331 A1 | 4/2015 | Wang et al. |
| 2015/0219615 A1 | 8/2015 | Nyadong et al. |
| 2017/0363602 A1 | 12/2017 | Koseoglu |
| 2018/0307803 A1 | 10/2018 | Watanasiri et al. |

FOREIGN PATENT DOCUMENTS

| | | |
|---|---|---|
| WO | 2013121204 A2 | 8/2013 |
| WO | 2016111988 A1 | 7/2016 |

OTHER PUBLICATIONS

Wei Wang, et al., "Detailed Chemical Composition of Straight-Run Vacuum Gas Oil and its Distillates as a Function of the Atmospheric Equivalent Boiling Point," Energy Fuels, 2016, 30 (2), pp. 968-974.

Diana Catalina Palacio Lozano et al., "APPI(+)-FTICR mass spectrometry coupled to partial least squares with genetic algorithm variable selection for prediction of API gravity and CCR of crude oil and vacuum residues," Fuel 2017 (193) pp. 39-44.

A.A. Al-Hajji, et al., "Characterization of Nitrogen and Sulfur Compounds in Hydrocracking Feedstocks by Fourier Transform Ion Cyclotron Mass Spectrometry," Oil & Gas Science & Technology, 63:1:115-128 (Dec. 31, 2008).

Muller Hendrik, et al., "Innate Sulfur Compounds as an Internal Standard for Determining Vacuum Gas Oil Compositions by APPI FT-ICR MS," Energy & Fuels, 34:7:8260-8273 (Jun. 12, 2020).

Tanner M. Schaub, et al., "Speciation of Aromatic Compounds in Petroleum Refinery Streams by Continuous low Field Desorption Ionization FT-ICR Mass Spectrometry," Energy & Fuels, 19:4:1566-1573 (Jul. 1, 2005).

PCT/US2020/038129, International Search Report and Written Opinion, dated Sep. 23, 2020, 16 pages.

SYSTEM AND METHOD OF CHARACTERIZING CRUDE OIL AND ITS DERIVATIVES BY COMBINING TOTAL SULFUR DETERMINATION AND FT-ICR MASS SPECTROMETRY

FIELD OF THE INVENTION

This invention relates to a system and method for the evaluation of samples of crude oil employing total sulfur determination and Fourier transform ion cyclotron resonance (FT-ICR) mass spectrometry (MS).

BACKGROUND OF THE INVENTION

Development and optimization of oil and gas downstream processes can benefit from knowing the feedstocks, intermediates and products, as well as their chemical transformations at the level of individual molecules. Such detailed information enables "molecular refining" that is tailored to the exact chemical composition of the feedstock and product slates.

Petroleum bulk properties are readily determinable; however, crude oil and its heavy fractions are highly complex hydrocarbon mixtures that remain difficult to characterize in molecular detail.

It is desirable to have quantitative compositional information about chemically well-defined compound groups and, ideally, for individual molecular species that comprise whole crude oil, its heavy fractions and products. This information would aid in the rational and efficient development of conversion processes, catalyst development and application, feedstock optimization, and selecting refining unit operations. However, prior art methods of quantitatively characterizing the composition of crude oil and its heavy fractions and products in this way are either not available or are severely limited. The current processes for modeling are based on the extrapolation of the compositional trends obtained from applying quantitative speciation of light and middle distillates, and on the direct measurement of bulk properties in the heavy fractions.

Current characterization approaches for petroleum crude oil can be grouped into three broad categories:

Quantitative Speciation of Light and Middle Distillates

To date, a compositional picture of a petroleum crude oil or its heavy fractions is extrapolated from the detailed speciation of the low- and mid-range boiling (light and middle, respectively) distillates based on group type separation, e.g., of diesel fuels, quantitative gas chromatographic analysis and comprehensive two-dimensional gas chromatography (GC×GC), respectively, and on bulk measurements of chemical and physical properties. The characterization of mid- to high-range boiling distillates such as light vacuum gas oils has been reported in the scientific literature; for hydrocarbons using GC×GC with flame ionization detection (FID), for sulfur-containing species using sulfur chemiluminescence detection (SCD), and with mass selective detection (MSD).

Bulk Properties

For real-world refining purposes, chemical bulk properties have been in use for decades for the characterization of heavy, that is, high or non-boiling, refinery feedstocks, interim- and final products. The boiling ranges of medium and heavy cuts, respectively, are routinely determined according to standardized methods to provide some information about the approximate molecular weight of the components. The quantification of heteroatom content, such as the total content of sulfur-containing compounds using x-ray spectroscopy, was developed in the early 1950s and remains in widespread use in the petroleum industry, as are methods for the quantitative determination of nitrogen-containing compounds and metals. Such bulk measurements express the measured element as elemental component and lack information about the actual percentage of the corresponding molecules. Determining the total sulfur content does, however, not directly represent the proportion of the molecules in a sample that are organosulfur compounds. For example, a vacuum gas oil sample with a total sulfur content of 2.7% wt (mass fraction of elemental sulfur) contains approximately 38% of organosulfur compounds if the average molecular weight is 450 Da. Such information is important for describing the sample as a feedstock for molecular level process modeling. Reliable quantitative data on group-type information such as the total mass fraction of saturated compounds ('saturates') or aromatic compounds ('aromatics') are difficult to obtain. For example, the classical fractionation into saturated, aromatic, resin, and asphaltene components (SARA analysis) does not address the chemical similarities between asphaltenes, resins, and aromatics, or issues such as entrained saturates in the aromatics fraction (and vice versa) that could be problematic from a process development/optimization perspective.

Qualitative Speciation of Crude Oils and Heavy Fractions and Products

The compositional analysis of high boiling fractions and non-boiling residues such as atmospheric and vacuum residues, and asphaltenes, etc., is established in the literature using high resolution mass spectrometry, predominantly using Fourier transform ion cyclotron resonance mass spectrometers. Depending on the target compounds, different modes of sample ionization have been employed; Hydrocarbon and/or sulfur aromatic species in VGO and VR samples have been reported using atmospheric pressure photo ionization (APPI), field desorption/field ionization (FD/FI), laser ionization, and selective derivatization. Polar compounds have been accessed using electrospray ionization (ESI), e.g., organic acids have been ionized via negative mode ESI and basic organic nitrogen species via positive mode ESI. However, with few exceptions addressed below, the data on heavy fractions and crude oil remains qualitative. Recently, efforts have been made to derive a detailed quantitative description (in form of a compositional model) of petroleum heavy ends through the measurement of the sample by several techniques, including multidimensional fractionation by liquid chromatography followed by high resolution mass spectrometry with multiple modes of ionization including FD/FI, APPI, ESI in positive and negative modes.

Despite the substantial advancements in instrumental analytical chemistry in the past decades, a comprehensive compositional characterization of petroleum crude oil remains incomplete at the near-molecular level. Specifically, methods that provide quantitative compositional information on crude oils, high- and non-boiling (heavy) petroleum fractions, and high- and non-boiling refined products are not available.

New rapid and direct methods to better determine the composition and properties from analysis of whole crude oil and its heavy fractions and products will save producers, marketers, refiners and/or other crude oil users substantial expense, effort and time. Therefore, a need exists for an improved system and method for determining such compositions and properties.

SUMMARY OF THE INVENTION

One embodiment is a method for evaluating a hydrocarbon oil sample and calculating a mass fraction of sulfur compounds and aromatic hydrocarbon compounds of the hydrocarbon oil sample, the method comprising:

providing a computer system that includes a processor coupled to non-volatile memory, determining total sulfur content of the hydrocarbon oil sample, and entering into the non-volatile memory the total sulfur content of the hydrocarbon oil sample, analyzing the hydrocarbon oil sample, subjected to solvent preparation, with a time-of-flight (TOF) mass spectrometer (MS) equipped with atmospheric pressure photo ionization (APPI) to obtain APPI TOF mass spectrometric data, entering the APPI TOF mass spectrometric data into the non-volatile memory, using the processor to calculate a molecular weight distribution and entering into the non-volatile memory the molecular weight distribution of the hydrocarbon oil sample;

analyzing the hydrocarbon oil sample with a Fourier transform ion cyclotron resonance (FT-ICR) mass spectrometer equipped with APPI, in which parameters on the FT-ICR mass spectrometer are tuned to reproduce the molecular weight distribution obtained in the analysis of the hydrocarbon oil sample with the TOF MS to obtain FT ICR mass spectrometric data, entering the FT-ICR mass spectrometric data into the non-volatile memory, using the processor to calculate a determination of elemental formulas and enter into the non-volatile memory the determination of elemental formulas of the hydrocarbon oil sample;

using the processor to calculate a mass fraction of sulfur compounds from the total sulfur content and the elemental formulas determination and enter into the non-volatile memory the mass fraction of sulfur compounds; and using the processor to calculate a mass fraction of aromatic hydrocarbon compounds from the mass fraction of sulfur compounds and from the elemental formula determination and entering into the non-volatile memory the mass fraction of aromatic hydrocarbon compounds.

In another embodiment as a method, the previous embodiment is supplemented by:

using the processor to calculate a mass fraction of saturated hydrocarbon compounds from the mass fraction of sulfur compounds and from the mass fraction of aromatic hydrocarbon compounds and entering into the non-volatile memory the mass fraction of saturated hydrocarbon compounds.

In another embodiment as a method, either of the previous embodiments is supplemented by:

using the processor to calculate an aromatic ring number families distribution from double-bond equivalent (DBE) values for each aromatic compound class and entering into the non-volatile memory the aromatic ring number families distribution, wherein the calculation is performed using the mass fraction of sulfur compounds, and using the mass fraction of aromatic hydrocarbon compounds.

In another embodiment as a method, any of the previous embodiments is supplemented by:

using the processor to calculate carbon number distributions for each aromatic ring number family and entering into the non-volatile memory the carbon number distributions for each aromatic ring number family, wherein the calculation is performed using the aromatic ring number families calculated from the DBE values for each compound class.

In another embodiment as a method, any of the previous embodiments is supplement by:

analyzing the hydrocarbon oil sample with oxidative combustion followed by chemiluminescence detection to obtain chemiluminescence data, entering the chemiluminescence data into the non-volatile memory, and using the processor to calculate a total nitrogen content of the hydrocarbon oil sample based upon the chemiluminescence data and enter into the non-volatile memory the total nitrogen content of the hydrocarbon oil sample, and using the processor to calculate a mass fraction of nitrogen compounds from the total nitrogen determination and the elemental formulas determination and enter into the non-volatile memory the mass fraction of nitrogen compounds.

In another embodiment as a method, any of the previous embodiments is supplemented by:

using the processor to calculate a mass fraction of saturated hydrocarbon compounds from the mass fraction of sulfur compounds, from the mass fraction of nitrogen compounds, and from the mass fraction of aromatic hydrocarbon compounds and enter into the non-volatile memory the mass fraction of saturated hydrocarbon compounds.

In another embodiment as a method, in the embodiment listed previously in which the hydrocarbon oil sample is analyzed with oxidative combustion followed by chemiluminescence detection to obtain chemiluminescence data, and in which the mass fraction of nitrogen compounds is calculated, the method is further supplemented by:

using the processor to calculate aromatic ring families distribution from double-bond equivalent (DBE) values for each aromatic compound class, wherein the calculation is performed using the mass fraction of sulfur compounds, the mass fraction of nitrogen compounds, and the mass fraction of aromatic hydrocarbon compounds and enter into the non-volatile memory aromatic ring families distribution.

In another embodiment as a method, the previous embodiment further comprises:

using the processor to calculate a carbon numbers distribution for each aromatic ring family and enter into the non-volatile memory carbon number distributions for each aromatic ring family, wherein the calculation is performed from the aromatic ring families calculated from the DBE values for each compound class.

In another embodiment as a method, the embodiment above in which the processor is used to calculate aromatic ring families distribution from double-bond equivalent values for each aromatic compound class, the method is further supplemented by:

using the processor to calculate a total alkyl chain length distribution for each aromatic ring family and enter into the non-volatile memory total alkyl chain length distributions for each aromatic ring family, wherein the calculation is performed from the aromatic ring families calculated from the DBE values for each compound class.

Another embodiment is a system for evaluating a hydrocarbon oil sample and calculating a mass fraction of sulfur compounds and aromatic hydrocarbon compounds of the hydrocarbon oil sample, the system comprising:

a non-volatile memory device that stores calculation modules and data;

a processor coupled to the non-volatile memory;

an X-ray fluorescence (XRF) spectrometer that analyzes the hydrocarbon oil sample to derive XRF spectrometric data, which is stored in the non-volatile memory;

a total nitrogen analyzer using oxidative combustion followed by chemiluminescence detection that analyzes the hydrocarbon oil sample to derive chemiluminescence spectrometric data, which is stored in the non-volatile memory;

a time-of-flight (TOF) mass spectrometer equipped with atmospheric pressure photo ionization (APPI), that analyzes the hydrocarbon oil sample to derive TOF mass spectrometric data, which is stored in the non-volatile memory;

a Fourier transform ion cyclotron resonance (FT-ICR) mass spectrometer equipped with APPI, that analyzes the hydrocarbon oil sample to derive FT-ICR mass spectrometric data, in which parameters of the FT-ICR mass spectrometer are tuned to reproduce the molecular weight distribution obtained from the TOF mass spectrometric data, and wherein the derived FT-ICR mass spectrometric data is stored in the non-volatile memory;

a first calculation module that, when executed by the processor, calculates a total sulfur content of the hydrocarbon oil sample based upon the XRF spectrometric data, and enters the calculated total sulfur content into the non-volatile memory;

a second calculation module that, when executed by the processor, calculates a molecular weight determination of the hydrocarbon oil sample from the TOF mass spectrometric data, and enters the calculated molecular weight distribution into the non-volatile memory;

a third calculation module that, when executed by the processor, produces a determination of elemental formulas of the hydrocarbon oil sample from the FT-ICR mass spectrometric data, and enters the calculated determination of elemental formulas into the non-volatile memory; and a fourth calculation module that, when executed by the processor, determines a mass fraction of sulfur compounds from the total sulfur content and the determination of elemental formulas, and enters the calculated mass fraction of sulfur compounds into the non-volatile memory;

a fifth calculation module that, when executed by the processor, determines a mass fraction of nitrogen compounds from the total nitrogen content and the determination of elemental formulas, and enters the calculated mass fraction of nitrogen compounds into the non-volatile memory; and a sixth calculation module that, when executed by the processor, calculates and enters into the non-volatile memory the mass fraction of aromatic hydrocarbon compounds from the mass fraction of sulfur compounds, and from the elemental formulas determination.

In another embodiment as a system, the previous embodiment is further supplemented by:

a seventh calculation module that, when executed by the processor, calculates and enters into the non-volatile memory a mass fraction of saturated hydrocarbon compounds from the mass fraction of sulfur compounds, from the mass fraction of nitrogen compounds, and from the mass fraction of aromatic hydrocarbon compounds.

In another embodiment as a system, either of the two previous system embodiments is supplemented by:

a eighth calculation module that, when executed by the processor, calculates and enters into the non-volatile memory aromatic ring number families from double-bond equivalent (DBE) values for each aromatic compound class, wherein the calculation is performed using the mass fraction of sulfur compounds, using the mass fraction of nitrogen compounds, and using the mass fraction of aromatic hydrocarbon compounds.

In another embodiment as a system, the previous embodiment further comprises:

a ninth calculation module that, when executed by the processor, calculates and enters into the non-volatile memory carbon numbers for each aromatic ring family, wherein the calculation is performed using the aromatic ring number families calculated from the DBE values for each compound class.

BRIEF DESCRIPTION OF THE DRAWINGS

Further advantages and benefits of the present invention will become apparent from the following detailed description of the invention when considered with reference to the accompanying drawings in which.

DETAILED DESCRIPTION OF INVENTION

Figure 1:
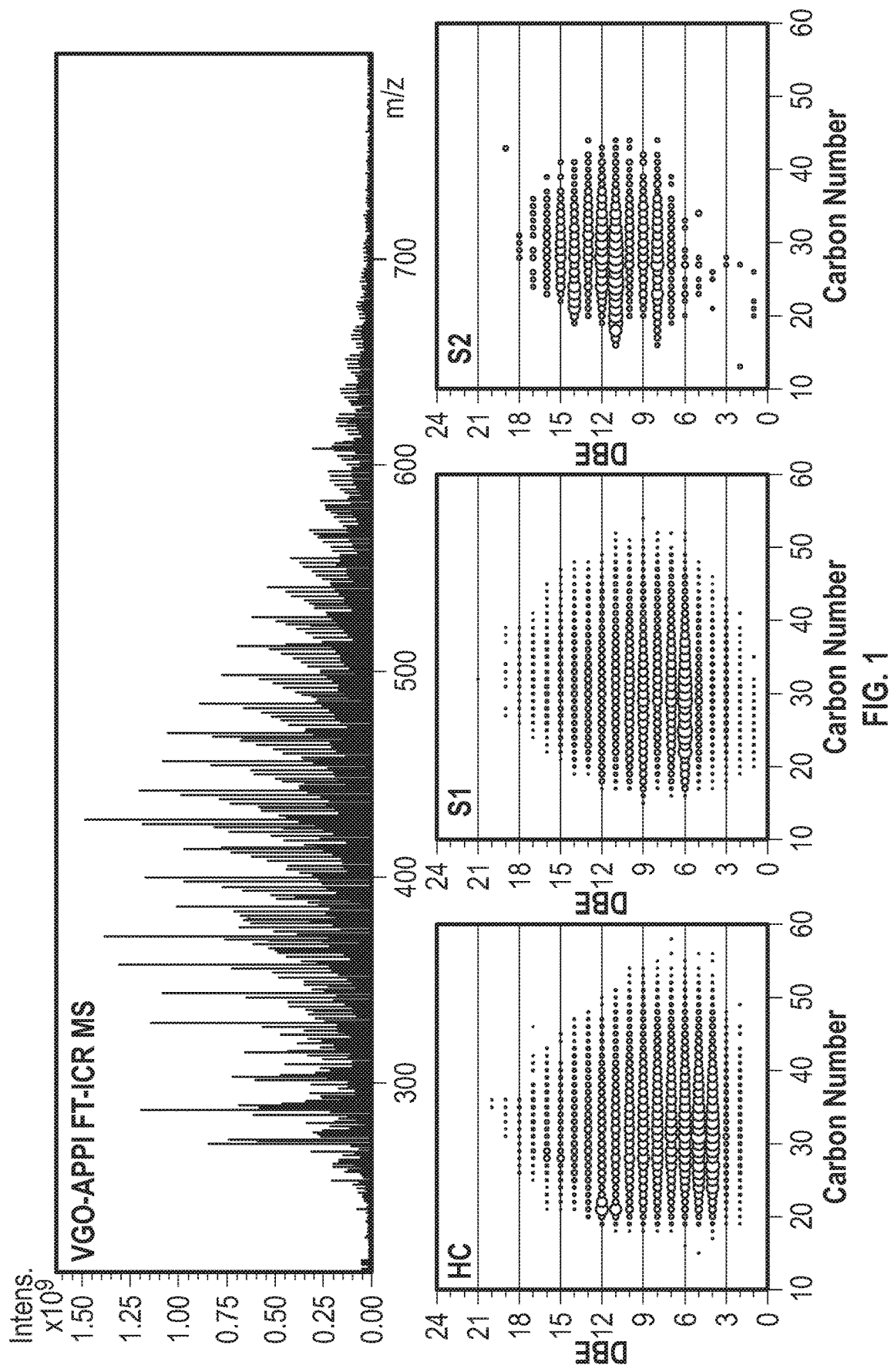
FIG. 1 is a series of plots depicting the mass spectrum of a vacuum gas oil sample and the identified class data obtained using APPI FT-ICR MS.

A system and method are provided for determining detailed compositional information for a hydrocarbon sample that includes the mass fraction of compounds (a) by heteroatom class, such as aromatic hydrocarbon compounds, sulfur-, sulfur-nitrogen-, and nitrogen-containing aromatic compound classes, (b) the distribution of aromatic ring number families in each of the heteroatom classes, that is, the number of aromatic rings in a molecule, and (c) the distribution of carbon atom numbers within each aromatic ring family. The mass fraction of the combined saturated compounds in the sample is also determined.

The present invention relates to a system and method for the determination of the composition of petroleum crude oils and high- and non-boiling fractions derived from crude oils, bitumens, heavy oils, shale oils and from refinery process units including hydrotreating, hydroprocessing, fluid catalytic cracking, coking, and visbreaking or coal liquefaction unit operations. Samples can be obtained from various sources, including a wellhead, a stabilizer, extractor, or from distillation towers.

The present system and method are employed to calculate the mass fraction of the principal components of the sample by combining data corresponding to the total sulfur content of the sample with the results of the detailed speciation obtained using high resolution mass spectrometry. The method and system make available:

1. the detailed mass fraction of aromatic hydrocarbons, sulfur, multi-sulfur, sulfur-nitrogen, and multi-sulfur-nitrogen containing aromatic compound classes present in the sample,
2. for each compound class the family distribution by number of aromatic rings per molecule,
3. for each aromatic ring number family (for all compound classes) the distribution of carbon numbers within that family.

4. Additionally, the mass fraction of the family of saturated compounds is derived as the remainder of the mass balance.

Our invention details, to our knowledge, the first combination of elemental bulk determination of sulfur for distribution on high resolution mass spectrometry data. It also embodies the first time that the aromatic hydrocarbon compounds are determined based on the atmospheric pressure photo ionization (APPI) response of sulfur-containing aromatic compounds. It also embodies the first time that aromatic compounds are determined by APPI FT-ICR MS and the saturated compounds are determined as a balance.

The system and method described in the present disclosure allows for the distribution of total heteroatom content among high resolution mass spectrometry data. The measured quantities pertain to total sulfur content distributed onto the sulfur-containing aromatic compounds.

In certain embodiments, the invention provides the measured quantities pertain to the sulfur-containing aromatic compounds with a plurality of sulfur atoms per molecule.

In certain embodiments, sulfur-containing compounds can include a plurality of nitrogen atoms.

In certain embodiments, the measured quantities pertain to the number of aromatic rings per sulfur-containing compounds (ring type families).

In certain embodiments, the measured quantities pertain to the number of carbon atoms in ring type families of sulfur-containing compounds.

In certain embodiments, the measured quantities pertain to total nitrogen content distributed onto the nitrogen-containing aromatic compounds.

In certain embodiments, the measured quantities pertain to the nitrogen-containing aromatic compound with a plurality of nitrogen atoms per molecule.

In certain embodiments, the measured quantities pertain to the number of aromatic rings per nitrogen-containing compounds (ring type families).

In certain embodiments, the measured quantities pertain to the number of carbon atoms in ring type families of nitrogen-containing compounds.

In certain embodiments, the system and method determines the total aromatic hydrocarbon content using high resolution mass spectrometry data based on the sulfur aromatic content and photo ionization response.

In certain embodiments, the measured quantities pertain to total aromatic hydrocarbon content distributed onto the aromatic hydrocarbon compounds.

In certain embodiments, the measured quantities pertain to the number of aromatic rings per aromatic hydrocarbon compound (ring type families).

In certain embodiments, the measured quantities pertain to the number of carbon atoms in ring type families of aromatic hydrocarbon compounds.

In certain embodiments, the system and method determines the total saturated hydrocarbon content using high resolution mass spectrometry data based on the sulfur aromatic content, aromatic hydrocarbon content, and photo ionization by difference.

FIG. 1 shows example of qualitative data obtained using a Bruker Daltonics APEX Qe FTMS equipped with a 9.4 T magnet and APPI source. The plots were created using in-house developed Visual Basic macros in Excel (Microsoft, Redmond, USA) after data reprocessing described in an illustrative example given below. The top graphic shows an example mass spectrum obtained for a vacuum gas oil sample, and below plots that show qualitative representations of the identified elemental formulas for this mass spectrum. The x-axis in these plots reflects for the number of carbon atoms per elemental formula and the y-axis is the value of the double bond equivalence (DBE) per formula, which is a measure of the rings and double bonds in the corresponding molecular structures. The area of the dots represents the mass spectral intensity of the corresponding molecular ion (including any identified isotopic signals). From left to right, the plots are displayed the pure hydrocarbon species (HC), that is, all elemental formulas that contain exactly no hetero atoms, mono-sulfur (S1) species, that is, elemental formulas that contain exactly one sulfur atom, and di-sulfur (S2) species, that is, elemental formulas that contain exactly two sulfur atoms.

Figure 2:
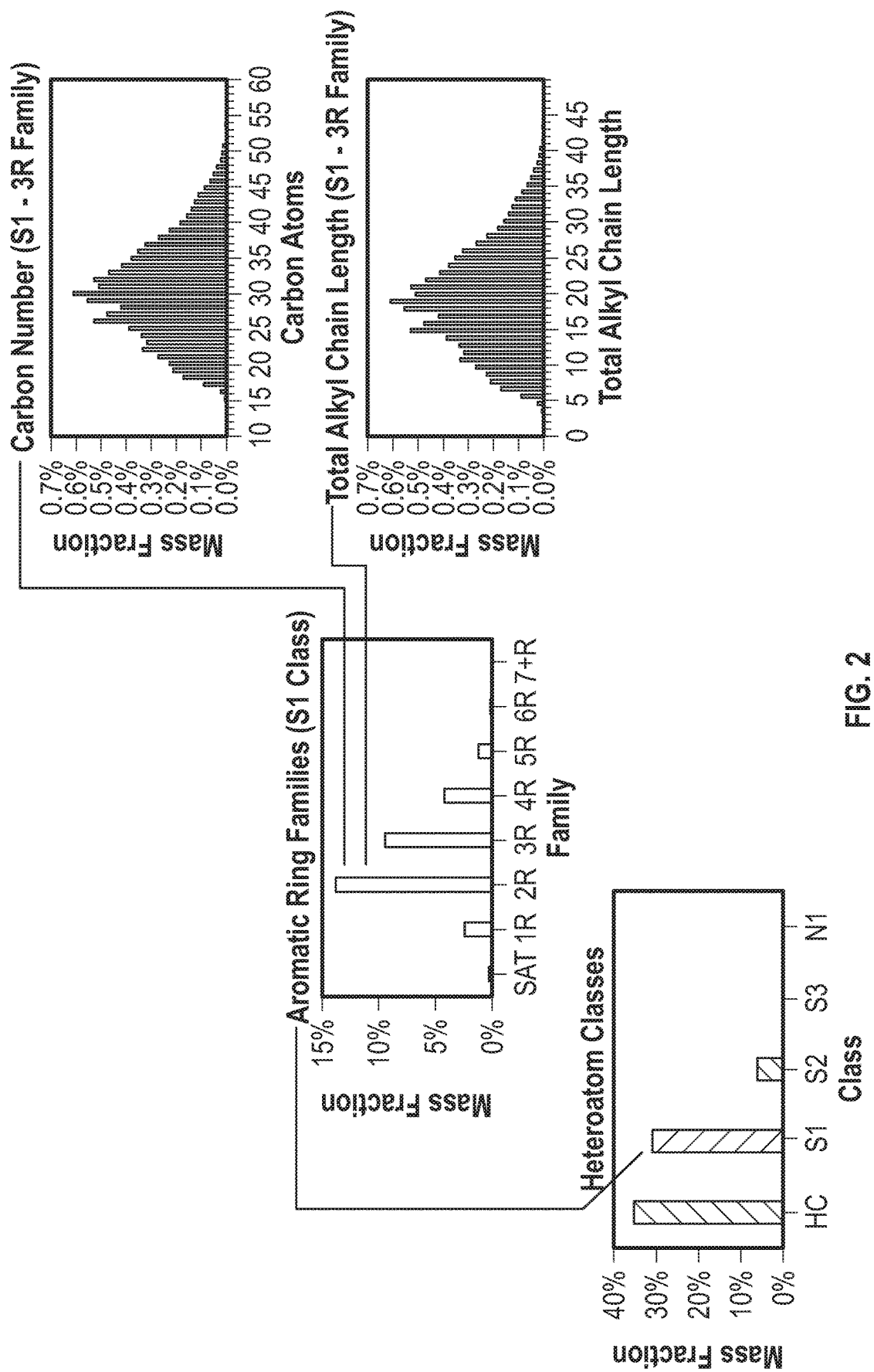
FIG. 2 is a series of plots of the Mass Fraction for various components showing the data structure obtained by the system and method herein.

FIG. 2 shows a hierarchical representation of the compositional information obtained using an embodiment disclosed herein: 1) Mass fractions of the heteroatom classes. 2) Mass fractions of the aromatic ring families of each heteroatom class on the example of the S1 class. 3) Mass fractions of the carbon numbers of each aromatic ring family on the example of the 3 ring family of the S1 class. 4) Mass fraction and total alkyl chain length of each aromatic ring family on the example of the 3 ring family of the S1 class.

Figure 3:
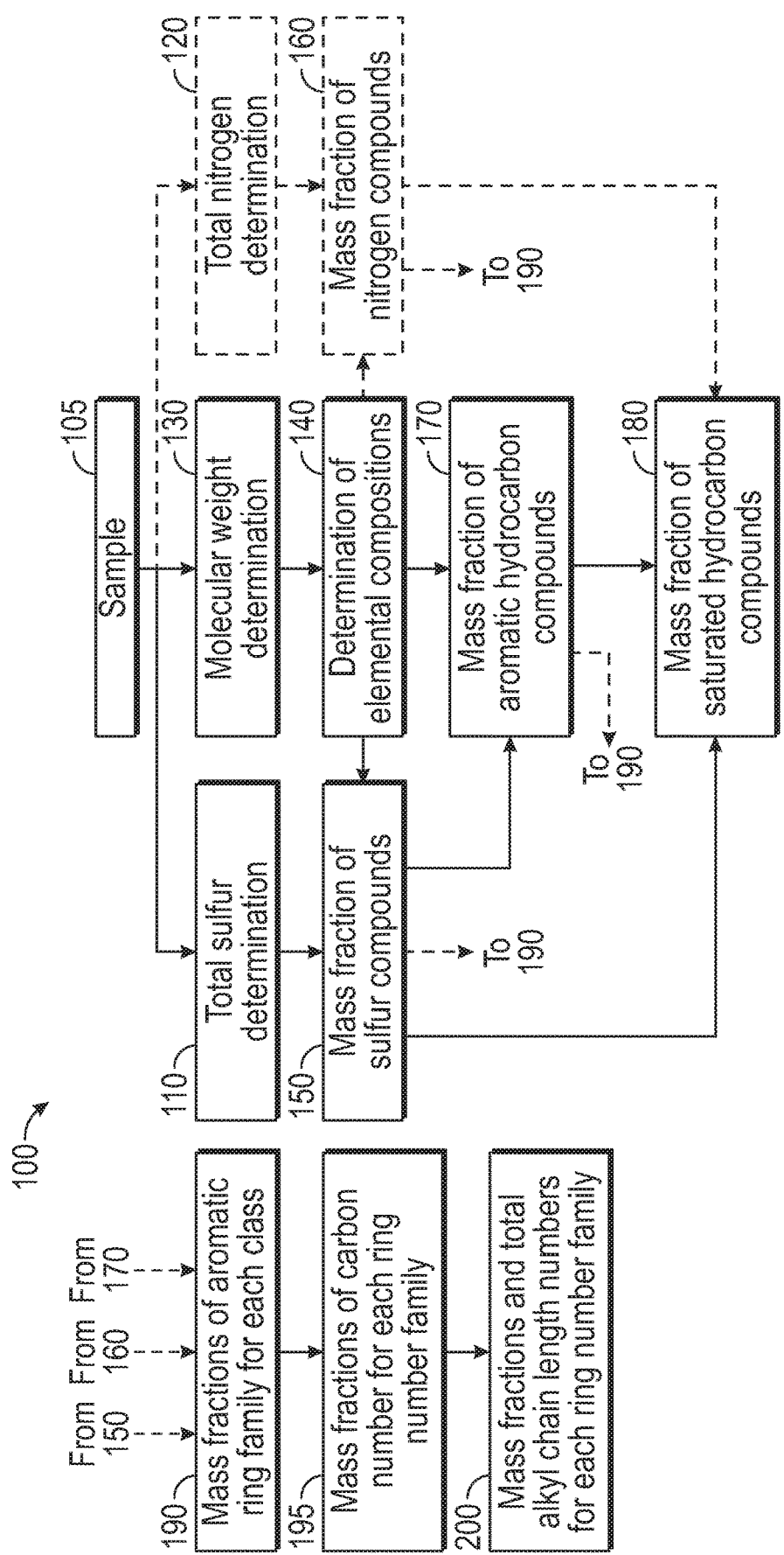
FIG. 3 is a process flow chart depicting steps to derive the compositional characterization of a hydrocarbon sample.

The schematic diagram of FIG. 3 illustrates an embodiment of a method 100 for determining the mass fractions of aromatic hydrocarbons (HC), and aromatic sulfur (S1), multi-sulfur ($S_s$, typically s=2 to 3 sulfur atoms, but could extend to 5 sulfur atoms), sulfur-nitrogen, and multi-sulfur-multi-nitrogen ($S_sN_n$, typically with s=1 to 3 sulfur atoms, and n=1 to 2 nitrogen atoms) heteroatom classes present in a sample. The method further determines details for each heteroatom class, including (a) the aromatic ring family distribution based on the number of aromatic rings per molecule, which in case of multi-ringed families includes fused and alkyl chain linked aromatic ring systems, (b) for each aromatic ring family the distribution of carbon numbers, (c) the distribution of total alkyl chain lengths within each aromatic ring number family, and (d) the mass fraction of saturated compounds is derived as the remaining mass balance. The method is applicable to hydrocarbon samples including but not limited to crude oil, vacuum gas oils, atmospheric residues, vacuum residues, asphaltenes, mid- and high-boiling products of hydrocracking/hydrotreating processes, and pyrolysis fuel oils.

In step 105, a hydrocarbon oil sample is obtained. Homogeneity of the sample is required. For some of the later steps, solvent preparation will be required, as described for those steps.

In step 110, total sulfur content is determined by a suitable method according to accepted industry standards, including x-ray fluorescence (XRF), for example ASTM D 2622, ASTM D4294, ASTM D 4927, ASTM D6334, ASTM D 6443, or ASTM D6445, or by combining combustion with various determination steps such as UV fluorescence, for example ASTM D5453, ASTM D6667, ASTM D7183, ISO 20846, coulometry, for example ASTM D3120, ASTM D3246, ASTM D3961, ASTM D6428, electrochemistry such as ASTM D6920, precipitation such as ASTM D129, wet chemistry such as ASTM D1266, iodate titration or IR detection according to ASTM D1552, or hydrogenolysis and colorimetry using ASTM D4045, or inductively coupled plasma atomic emission spectrometry such as ASTM D4951 or ASTM D5185.

In optional step 120, total nitrogen content is determined by a suitable standard method, such as ASTM D4629, ASTM D5291, ASTM D5762, ASTM D6069, ASTM D7184 or equivalent. Some crude oils, such as Saudi Arabian Extra Light or those from Texas, are known to have little, if any nitrogen, so that this step (120) can be omitted. Other crude oils, such as those from South America, are known to contain significant portions of nitrogen, so for those crude oils and their fractions, step 120 is important.

The cited standard methods (except for ASTM D5291) rely on the oxidative combustion of the sample followed by chemiluminescence detection. ASTM D5291 relies on the combustion of the sample, followed by a reduction of the NOx in the exhaust gas to N2 gas and its subsequent gas chromatographic separation and detection using a thermal conductivity detector.

In step 130, a molecular weight (MW) distribution of the sample is determined by performing a mass spectrometric analysis with a time-of-flight (TOF) mass spectrometer (MS) equipped with atmospheric pressure photo ionization (APPI). The hydrocarbon sample is prepared for step 130 to achieve a sample solution that can be directly infused into the APPI source of a mass spectrometer using a syringe pump. A suitable solvent for preparing the sample can be a C6-C8 aromatic hydrocarbon, with toluene being the preferred solvent. In certain embodiments, the aromatic hydrocarbon is combined with a polar solvent, for instance selected from the group consisting of methanol, methylene chloride (DCM), and tetrahydrofuran. The final dilution ratio depends on the sample and has to be checked on a case-by-case basis. Typically, a sample is diluted at ratios between 1:1,000 and 1:1,000,000.

In step 140, the composition of the sample expressed as elemental formulas is determined by performing a mass spectrometric analysis with an FT-ICR MS equipped with APPI. For step 140, the stock solution of the sample is diluted to at least 0.1 mg/mL in an aromatic hydrocarbon, with toluene being the preferred solvent for direct infusion into the APPI source of the FT-ICR MS. A complete solubility must be attained (no precipitate visible); otherwise, a polar solvent, for instance selected from the group consisting of methanol, methylene chloride (DCM), and tetrahydrofuran, must be added until the solution is deposit free. In this step, the parameters are tuned to reproduce the MW distribution obtained in step 130 with the TOF MS. The FT-ICR MS raw data is recorded, mass calibrated based on present component series, and elemental formulas are assigned considering only molecular ion species for HC, S1, S2, S3, N1, S1N1, S2N1, S3N1, N2, S1N2, S2N2, and S3N2 species.

The order in which steps 110 through 140 are performed is not deemed to be critical, except that step 130 is to be performed prior to step 140.

In step 150, the mass fraction of sulfur compounds is calculated. First, the total sulfur content is distributed among sulfur species identified by FT-ICR MS. The summed relative abundance (A) of each double-bond equivalent (DBE) series of each sulfur containing class (S1, S2, S3, S1N1, etc.) determined in step 140 is calculated by adding the APPI mass spectral abundance of all its associated species over the combined mass spectral abundance of all species to produce $A_{S1_{DBE}}$, $A_{S2_{DBE}}$, $A_{S3_{DBE}}$, and $A_{S1N1_{DBE}}$, etc., with DBE indicating the specific DBE value of the series.

The value of each A is then multiplied by the number of sulfur atoms in the class, and normalized on the combined total of all sulfur containing classes using equation 1:

$$\hat{A}_{SsNn_{DBE}} = \frac{A_{SsNn_{DBE}}}{\sum_{s=1}^{3}\sum_{n=0}^{1}\sum_{DBE=0}^{40}\left(A_{SsNn_{DBE}} \times s\right)}; \quad (1)$$

where:

s represents the number of sulfur atoms, such that S1 is a mono-sulfur species, S2 is a di-sulfur species, and S3 is a tri-sulfur species, and n represents the number of nitrogen atoms.

Equation 1 accounts for the different numbers of sulfur atoms in each class and results in a sulfur-normalized relative abundance ($\hat{A}$).

In order to calculate the classes' (DBE series') total sulfur (TS) equivalent ($\widetilde{TS}_{SsNn_{DBE}}$) that is, how much does the particular class (DBE series) contribute to the TS, the total sulfur content, expressed as mass fraction, is multiplied by the value of each classes' (or DBE series') $\hat{A}$.

The weight-averaged molecular weight (M) is then calculated for each DBE series of each sulfur-containing class. First, the weighted average carbon numbers ($C\#_{DBE}$) are calculated from the elemental composition data obtained by APPI FT-ICR MS, as follows. For each DBE series (and each class), the individual carbon numbers are multiplied by its corresponding mass spectral abundance, all values in the DBE series are summed, and the sum is divided by the DBE series' summed mass spectral intensity. This weighted average carbon numbers ($C\#_{DBE}$) are then used to calculate the weight-averaged molecular weight (M), using equation 2:

$$M_{SsNn_{DBE}} = C\#_{DBE} \times 12 + \quad (2)$$
$$\left(C\#_{DBE} - DBE + 1 + \frac{n}{2}\right) \times 2 \times 1.007825 + s \times 31.972070 + n \times 14.003074;$$

Finally, the mass fraction (WT) of each sulfur containing DBE series is obtained by dividing its $\widetilde{TS}_{SsNn_{DBE}}$ by the monoisotopic atomic weight of sulfur and multiplying by its $M_{SsNn_{DBE}}$, as shown in equation 3. $\widetilde{TS}_{SsNn_{DBE}}$ is the mass fraction of total sulfur content held by each DBE series of the sulfur containing classes. In other words, $\widetilde{TS}_{SsNn_{DBE}}$ accounts for how much sulfur a DBE series 'contains', expressed as total sulfur content (that is, its contribution to the mass fraction of elemental sulfur). Equation 3 describes the conversion of the mass fraction of total sulfur (that is, elemental sulfur, 32S) to the mass fraction of organic molecules that contain at least one sulfur atom. This conversion requires the molecular weight of the organic sulfur containing compounds ($M_{SsNn_{DBE}}$)

$$WT_{SsNn_{DBE}} = \frac{\hat{ts}_{SsNn_{DBE}}}{31.972070} \times M_{SsNn_{DBE}}. \quad (3)$$

In a case where optional step 120 is performed, optional step 160 is applied to calculate the mass fraction of nitrogen compounds from the total nitrogen determination of step 120 and the elemental composition determination of step 140. Analogously to step 150, which describes the calculation of the mass fraction of sulfur containing heteroatom classes (and all their respective DBE series) based on the total sulfur content, the mass spectral abundances, the number of sulfur atoms per class, and the weighted average molecular weight of each sulfur containing classes' DBE series, step 160 describes the calculation of the mass fraction of nitrogen containing heteroatom classes (and all their respective DBE series) based on the total nitrogen content, the mass spectral abundances (obtained using APPI), the number of nitrogen atoms per class, and the weighted average molecular weight of each nitrogen containing classes' DBE series. The monoisotopic mass of nitrogen ($^{14}$N with amu 14.00307) is used.

In step 170, the mass fraction of aromatic hydrocarbon species is determined. First, the mass fraction of the aromatic hydrocarbon species is calculated by multiplying $WT_{S1}$ by the ratio of the summed relative abundances of $A_{S1}$ and $A_{HC}$ as shown in equation 4:

$$WT_{HC} = WT_{S1} \times \frac{A_{Hc}}{A_{S1}};\qquad(4)$$

Note that nitrogen is not shown in equation 4. The calculation of aromatic hydrocarbons, step 170, must be based solely on the aromatic sulfur species, because only those have comparable response factors. Nitrogen-containing aromatic species can vary in their polarity between "neutral" pyrrole based aromatic molecules (containing nitrogen in form a 5-membered ring) and "basic" pyridine based aromatic molecules (containing nitrogen in form of a 6 membered rings). Both forms of nitrogen containing molecules are known to vary much wider in respect to their ionization behavior and, therefore, do not qualify as reference for direct quantification.

This calculation is founded on the chemical similarity of sulfur and hydrocarbon aromatic species relative to photoionization.

Then, $WT_{HC}$ is distributed on the hydrocarbon DBE series based on their relative summed abundances ($A_{HC_{DBE}}$) The hydrocarbon aromatic ring number abundances are calculated analogously to those of sulfur-containing compounds, see Table 1.

TABLE 1

DBE Values to be Combined by Number of Aromatic Rings.

| #AROMATIC RINGS | HC | S1 | S2 | S3 | N1 |
|---|---|---|---|---|---|
| 0 | 0-3 | 0-2 | 0-2 | 0-2 | −0.5-2.5 |
| 1 | 4-6 | 3-5 | 3-4 | 3-4 | 2.5-4.5 |
| 2 | 7-9 | 6-8 | 5-7 | 5-6 | 5.5-7.5 |
| 3 | 10-12 | 9-11 | 8-10 | 7-9 | 8.5-10.5 |
| 4 | 13-15 | 12-14 | 11-13 | 10-12 | 11.5-13.5 |
| 5 | 16-18 | 15-17 | 14-16 | 13-15 | 14.5-16.5 |
| 6 | 19-21 | 18-20 | 17-19 | 16-18 | 17.5-19.5 |
| 7+ | 22+ | 21+ | 20+ | 19+ | 20.5+ |

In step 180, the mass fraction of saturated hydrocarbon species is calculated. Saturated compounds cannot be detected directly and are, therefore, calculated as the difference of the total sample minus the sum of all known and determined aromatic species. Hence, the bulk weight fraction of saturated compounds is calculated as shown in equation 5:

$$WT_{Sat}=1-(WT_{HC}+WT_{S1}+WT_{S2}+WT_{S3}+WT_{S1N1}\ldots)\qquad(5);$$

In step 190, the distribution of aromatic rings is determined, using the input from steps 150, 170, and optional step 160, if performed. The mass fractions of individual DBE series are summed, depending on the class, to derive the summed mass fraction per number of aromatic rings. Table 1 lists the DBE series that must be combined to reflect the number of aromatic rings given in the left column.

Summing $WT_{S1_{DBE}}$ over all DBE series produces the combined mass fraction of mono-sulfur species. Similarly, the summed mass fractions of the remaining sulfur containing classes (S2, S3, S1N1, etc.) can be obtained.

In step 195, carbon numbers are calculated for each aromatic ring family. Based on the individual mass spectral abundances corresponding to the elemental formulas obtained in step 140, the mass fractions of each aromatic ring family are distributed among its members, to provide the mass fraction breakdown per carbon number. For this disclosure, the DBE series corresponding to the aromatic ring family as shown in Table 1 are combined to calculate the carbon number distribution.

In step 200, the total alkyl chain length for each aromatic ring family are calculated. The number of carbon atoms in aromatic rings that are listed in Table 2 for typical heteroatom classes, are subtracted from the carbon numbers discussed in step 195.

TABLE 2

Carbon Atoms in Aromatic Rings per Aromatic Ring Family.

| #AROMATIC RINGS | HC | S1 | S2 | S3 | N1 |
|---|---|---|---|---|---|
| 0 | 0 | 0 | 0 | 0 | 0 |
| 1 | 6 | 4 | 4 | 4 | 4 |
| 2 | 10 | 8 | 6 | 6 | 8 |
| 3 | 14 | 12 | 10 | 8 | 12 |
| 4 | 18 | 16 | 14 | 12 | 16 |
| 5 | 22 | 20 | 18 | 16 | 20 |
| 6 | 26 | 24 | 22 | 20 | 24 |
| 7+ | 32 | 28 | 26 | 24 | 28 |

Table 3 provides a list of abbreviations used in equations 1 through 5.

TABLE 3

List of Abbreviations Used in Calculations

| Abbreviation | Definition |
|---|---|
| HC | Hydrocarbon species |
| S1 | Mono-sulfur species |
| S2 | Di-sulfur species |
| S3 | Tri-sulfur species |
| S1N1 | Nitrogen-sulfur species |
| SsNn | Class with s sulfur and n nitrogen atoms |
| A | Summed relative abundance |
| $A_{S1}$ | Summed relative abundance of the annotated class (mono-sulfur species) |
| $A_{S1_{DBE}}$ | Summed relative abundance of the annotated class (mono-sulfur species) and the specific DBE value |
| TS | Total sulfur content |
| Â | Total sulfur-equivalent relative abundance |
| $\hat{TS}_{SsNn_{DBE}}$ | Total sulfur equivalent for a given class and DBE series |
| M | Weighted average molecular weight |
| $M_{SsNn_{DBE}}$ | Weighted average molecular weight of a given class and DBE series |
| C# | Weighted average carbon number |
| $C\#_{DBE}$ | Weighted average carbon number of a given DBE series |
| WT | Weight fraction |
| $WT_{Sat}$ | Weight fraction of saturated hydrocarbon species |

To illustrate the process, a typical sample of a VGO Hydrocracker Feedstock, named "VGO (HCR FEED)" will now be discussed as example:

In step 105, the sample was diluted to a concentration of 10 mg/mL in toluene. The mixture was rigorously shaken by vortex mixer at more than 2000 rotations per minute for at least 30 seconds. A complete solubility was attained (no precipitate visible); otherwise, methylene chloride or another polar solvent would have been added until the solution was deposit free. This stock solution was diluted 1:10 in toluene to a concentration of approximately 1 mg/mL for the direct infusion into the APPI source of the TOF MS instrument.

In step 110, the total sulfur content was determined to be 2.710% wt according to ASTM D4294.

In step 120, the total nitrogen content was determined to be 596 ppmwt according to ASTM D4629.

In step 130, the TOF MS measurement is performed using an Agilent Technology G6230B time of flight mass spectrometer equipped with APPI source and parameters adjusted by a typically skilled person in the art. Specifically, the APPI furnace temperature was set to 400° C. and drying gas temperature to 300° C., respectively. Nitrogen gas flow rate in the nebulizer was set to 8 L min$^{-1}$ and the dry gas pressure to 40 psig, respectively. Ion source potentials were set to 3.0 kV for the capillary, fragmentor and skimmer to 150 V and 65 V, respectively. Ions were guided through an octapol with RF voltage at 750 Vpp. Mass spectra were collected from 100 m/z to 3,000 m/z, with approx. 9900 transients averaged per spectrum (1 s$^{-1}$), accumulated for 1 min and finally summed into a single extracted mass spectrum (Masshunter software, Agilent Technologies).

In step 140, high resolution mass spectra are acquired using a 9.4 T Apex Qe Fourier transform ion cyclotron resonance mass spectrometer (Bruker Daltonics, Bremen, Germany) with an Apollo II ion source in positive APPI mode. The stock solution was diluted 1:100 in toluene to a concentration of approximately 0.1 mg/mL for the direct infusion into the APPI and delivered by a syringe pump at a flow rate of 20 µL/min. Gas flow rates (nebulizer and dry gas) were set to 3 L/min. APPI furnace temperature was set to 400° C. and the drying temperature to 200° C. Ion source potentials were set as follows: Capillary: 1.5 kV, spray shield: 1.0 kV, capillary exit: 270 V. Molecular ions were guided through two skimmer/ion funnels with RF voltage set to 190 V and accumulated in an rf-only hexapole for 0.4 s. The quadrupole (q1) and hexapole collision cell (h2) were operated as ion guides, i.e., in rf-only mode only, before injection of the ion package into the ICR cell for high resolution, high accuracy mass measurement. The ion transfer time was adjusted to 1.0 ms. 128 scans with 4M data points were accumulated on ApexControl software (Bruker Daltonics, Bremen, Germany) for the high resolution mass spectrum and processed using DataAnalysis (Bruker Daltonics, Bremen, Germany) for peak picking with signal to noise ratio of 3. External mass calibration was conducted using HP Tune mix solution (5 mMolar in water/methanol 1:4) in positive mode electrospray. Internal calibration for the sample measurement was based on homolog series of aromatic hydrocarbons and sulfur containing compounds present in the sample. Elemental composition assignments of selected mass signals were confirmed by their isotopic fine structure. Elemental compositions (CcHhNnOoSs) were calculated for all mass signals using Composer software (ver. 1.0.5, SierraAnalytics, Modesto, Calif., USA) and plotted using in-house developed Visual Basic macros in Excel (Microsoft, Redmond, USA).

The summed relative abundance of each double-bond equivalent (DBE) series of the sulfur containing classes $A_{SsNn_{DBE}}$ are listed in Table 4.

TABLE 4

List of Relative Abundance (by APPI FT-ICR MS) per DBE series and per Heteroatom Class. The last row gives the Total Relative Abundance per Heteroatom Class.

| DBE | S1 | HC | S2 | N1 |
|---|---|---|---|---|
| 0 | 0.00011 | 0.00000 | 0.00000 | 0.00000 |
| 1 | 0.00272 | 0.00000 | 0.00427 | 0.00000 |
| 2 | 0.00576 | 0.00829 | 0.00224 | 0.00000 |
| 3 | 0.01668 | 0.01581 | 0.00230 | 0.00000 |
| 4 | 0.02028 | 0.14302 | 0.00335 | 0.00000 |
| 5 | 0.03925 | 0.14705 | 0.00806 | 0.00000 |
| 6 | 0.22865 | 0.12122 | 0.01293 | 0.00000 |
| 7 | 0.13008 | 0.10642 | 0.04166 | 0.00000 |
| 8 | 0.08016 | 0.09598 | 0.13323 | 0.00569 |
| 9 | 0.13115 | 0.09215 | 0.07594 | 0.10416 |
| 10 | 0.09847 | 0.07289 | 0.05721 | 0.11586 |
| 11 | 0.07078 | 0.05977 | 0.22101 | 0.15306 |
| 12 | 0.06075 | 0.05396 | 0.14420 | 0.19999 |
| 13 | 0.04256 | 0.03101 | 0.07270 | 0.14971 |
| 14 | 0.03100 | 0.02019 | 0.10395 | 0.10661 |
| 15 | 0.01901 | 0.01451 | 0.06471 | 0.08214 |
| 16 | 0.01202 | 0.01001 | 0.03038 | 0.05522 |
| 17 | 0.00623 | 0.00487 | 0.01432 | 0.02139 |
| 18 | 0.00296 | 0.00172 | 0.00504 | 0.00616 |
| 19 | 0.00116 | 0.00087 | 0.00105 | 0.00000 |
| 20 | 0.00000 | 0.00026 | 0.00000 | 0.00000 |
| Summed Relative Abundance | 0.43589 | 0.50449 | 0.04300 | 0.01663 |

In step 150, the mass fraction of sulfur compounds is distributed among sulfur containing heteroatom classes according to their summed relative abundances as listed in Table 4. For this, the summed relative abundance is multiplied by the number of sulfur atoms in the class, and normalized on the combined total of all sulfur containing classes using equation 1. For the S1 class as example, with the denominator of equation 1:

$\Sigma_{S=1}^{3}\Sigma_{n=0}^{1}\Sigma_{DBE=0}^{40}(A_{SsNn_{DBE}} \times s) = 0.5219$.

The relative total sulfur content of the S1 class equation 1 resolves to:

$$\hat{A}_{S1} = \frac{0.43589}{0.5219} = 0.8352.$$

With a total sulfur content (mass fraction of 2.710%), determined in step 110, the equivalent total sulfur content of class S1 ($\overline{TS}_{S1}$) is:

$\overline{TS}_{S1} = 2.710\% \text{ wt} \times 0.8352 = 2.26\%$.

The S2 class calculations follow the same principle, results are summarized in Table 5, including nitrogen which is calculated separately in step 160.

TABLE 5

Calculation details of the total sulfur and total nitrogen-equivalent relative abundances for sample VGO (HCR FEED).

| | EXPLANATION | S1 | S2 | N1 | HC |
|---|---|---|---|---|---|
| A | Summed relative abundance | 0.43589 | 0.04300 | 0.01663 | 0.50449 |
| s | Sulfur atoms per molecule | 1 | 2 | 0 | 0 |
| A * s | | 0.43589 | 0.08599 | | |
| Â | Total sulfur-equivalent relative abundance | 0.8352 | 0.1648 | | |
| $\overline{TS}$ | Total sulfur equivalent for given class | 2.26% | 0.45% | | |

TABLE 5-continued

Calculation details of the total sulfur and total nitrogen-equivalent relative abundances for sample VGO (HCR FEED).

| | EXPLANATION | S1 | S2 | N1 | HC |
|---|---|---|---|---|---|
| n | Nitrogen atoms per molecule | 0 | 0 | 1 | 0 |
| A * n | | | | 0.01663 | |
| $\overline{TN}$ | Total nitrogen equivalent for given class | | | 0.0060% | |

Further in step 150, the weight-averaged molecular weight (M) of the S1 class is then calculated from the weighted average carbon number (C#=30.43) and the weight average DBE value (DBE=8.59), both obtained from the elemental composition data by APPI FT-ICR MS in step 140, using equation 2:

$M_{S1}$=30.43×12+(30.43−8.59+1)×2×1.007825+1× 31.972070=443.2

Finally, the mass fraction (WT) of the S1 class is obtained, using equation 3, by dividing $\overline{TS}_{S1}$(=2.26%) by the monoisotopic atomic weight of sulfur (31.972070 Da) and multiplying by $M_{S1}$(=443.2 Da), using equation 3:

$$WT_{S1} = \frac{2.26\%}{31.972070} \times 443.2 = 31.35\%$$

Further in step 150, the weight-averaged molecular weight (M) of the S2 class is calculated from the weighted average carbon number (C#=28.80) and the weight average DBE value (DBE=11.17), both obtained from the elemental composition data by APPI FT-ICR MS in step 140, using equation 2:

$M_{S2}$=28.80×12+(28.80−11.17+1)×2×1.007825+2× 31.972070=447.1

Finally, the mass fraction (WT) of the S2 class is obtained, using equation 3, by dividing $\overline{TS}_{S2}$(=0.45%) by the monoisotopic atomic weight of sulfur (31.972070 Da) and multiplying by $M_{S2}$(=447.1 Da), using equation 3:

$$WT_{S2} = \frac{0.45\%}{31.972070} \times 447.1 = 6.24\%$$

In step 160, nitrogen is processed analogously to sulfur in step 150. In this example, the summed relative abundance of the N1 heteroatom class is multiplied by 1 (the number of nitrogen atoms in each molecule in this class). Because only one nitrogen containing heteroatom class is detected, normalization on the combined total of all nitrogen containing classes using equation 1 is not required.

Then, the monoisotopic mass of nitrogen (14.00307 Da) is used in equation 2 to calculate the weight-averaged molecular weight (M) of the N1 class from the weighted average carbon number (C#=29.24) and the weight average DBE value (DBE=12.25), both obtained from the elemental composition data by APPI FT-ICR MS in step 140:

$M_{N1}$=29.24×12+(29.24−12.25+1+½)×2×1.007825+1× 14.00307=401.1

The mass fraction (WT) of the N1 class is obtained, using equation 3, by dividing $\overline{TN}_{N1}$ (=0.0060%) by the monoisotopic atomic weight of nitrogen (14.00307 Da) and multiplying by $M_{N1}$(=401.1 Da), using equation 3:

$$WT_{N1} = \frac{0.0060\%}{14.00307} \times 401.1 = 0.17\%$$

In step 170, the mass fraction of aromatic hydrocarbon compounds is determined. First, the mass fraction of the aromatic hydrocarbon species is calculated by multiplying $WT_{S1}$=31.35% by the ratio of the summed relative abundances of $A_{S1}$=0.43589 and $A_{HC}$=0.50449 (compare data in Table 5, row 1) as shown in equation 4:

$$WT_{HC} = 31.35\% \times \frac{0.50449}{0.43589} = 35.07\%$$

In step 180, the mass fraction of saturated hydrocarbon species ($WT_{sat}$) is calculated. Saturated compounds are not detected by APPI FT-ICR MS in step 140, and make up the remaining mass fraction of the total sample minus the sum of all aromatic species determined in steps 150, 160, and 170, using equation 5:

$WT_{Sat}$=100%−(31.35%+6.24%&+0.17%+ 35.07%)=27.17%

The results for all classes in sample VGO (HCR FEED) are summarized in Table 6. Because saturated compounds are not detected by APPI FT-ICR MS in step 140 there weight-averaged molecular weight is not included.

TABLE 6

Weight averaged molecular weights of sulfur and nitrogen-containing classes and aromatic hydrocarbon compounds, and mass fractions for all compound classes, including saturated hydrocarbons, in sample VGO (HCR FEED).

| | EXPLANATION | S1 | S2 | N1 | HC(ARO) | HC(SAT) |
|---|---|---|---|---|---|---|
| M | weight-averaged molecular weight [Da] | 443.2 | 447.1 | 401.1 | 439.0 | — |
| WT | mass fraction | 31.35% | 6.24% | 0.17% | 35.07% | 27.17% |

In step 190, following steps 150, 160, and 170, the individual mass fractions per aromatic ring families are calculated for all aromatic compound classes. For this, the weight-averaged molecular weights for the individual DBE series are calculated in using equation 2, with the C# data for each classes' DBE series' values obtained in step 140. The distribution of aromatic rings is determined, using the input from steps 150, 160, and 170, whereby the mass fractions of individual DBE series are summed according to Table 1, depending on the class, to derive the summed mass fraction per number of aromatic rings. Data ($C\#_{S1_{DBE}}$ and $M_{S1_{DBE}}$) and results for the S1 class are listed in Table 7. S2, N1 and HC class data and results are listed in Table 8, 9, and 10, respectively.

TABLE 7

DBE, weighted average carbon number, weighted average molecular weight, mass fraction per DBE, aromatic ring family and mass fraction of aromatic ring families for S1 class of sample VGO (HCR FEED).

| DBE | C# | M | Mass Fraction | S1 Aromatic Ring Family | Mass Fraction |
|---|---|---|---|---|---|
| 0 | | | 0.00% | SAT | 0.26% |
| 1 | 26.52 | 403.6 | 0.08% | | |
| 2 | 29.39 | 441.9 | 0.18% | | |
| 3 | 29.68 | 444.0 | 0.52% | 1R | 2.42% |
| 4 | 30.70 | 456.3 | 0.65% | | |
| 5 | 30.20 | 447.1 | 1.24% | | |
| 6 | 29.21 | 431.3 | 6.98% | 2R | 13.81% |
| 7 | 30.88 | 452.7 | 4.17% | | |
| 8 | 32.30 | 470.5 | 2.67% | | |
| 9 | 29.64 | 431.3 | 4.00% | 3R | 9.37% |
| 10 | 30.71 | 444.3 | 3.09% | | |
| 11 | 31.53 | 453.7 | 2.27% | | |
| 12 | 30.06 | 431.1 | 1.85% | 4R | 4.16% |
| 13 | 31.18 | 444.8 | 1.34% | | |
| 14 | 31.21 | 443.2 | 0.97% | | |
| 15 | 31.77 | 449.0 | 0.60% | 5R | 1.19% |
| 16 | 32.33 | 454.8 | 0.39% | | |
| 17 | 32.08 | 449.4 | 0.20% | | |
| 18 | 32.23 | 449.5 | 0.09% | 6R | 0.13% |
| 19 | 33.26 | 461.8 | 0.04% | | |
| 20 | | | 0.00% | | |
| 21 | | | 0.00% | 7 + R | 0.00% |

TABLE 8

DBE, weighted average carbon number, weighted average molecular weight, mass fraction per DBE, aromatic ring family and mass fraction of aromatic ring families for S2 class of sample VGO (HCR FEED).

| DBE | C# | M | Mass Fraction | S2 Aromatic Ring Family | Mass Fraction |
|---|---|---|---|---|---|
| 0 | | | 0.00% | SAT | 0.03% |
| 1 | 22.40 | 377.9 | 0.02% | | |
| 2 | 20.15 | 344.3 | 0.01% | | |
| 3 | 27.54 | 445.9 | 0.01% | 1R | 0.03% |
| 4 | 24.31 | 398.6 | 0.02% | | |
| 5 | 27.44 | 440.5 | 0.05% | 2R | 0.39% |
| 6 | 26.45 | 424.6 | 0.08% | | |
| 7 | 28.70 | 454.1 | 0.26% | | |
| 8 | 28.38 | 447.6 | 0.83% | 3R | 1.72% |
| 9 | 30.31 | 472.6 | 0.50% | | |
| 10 | 31.03 | 480.7 | 0.38% | | |
| 11 | 26.90 | 420.9 | 1.30% | 4R | 2.70% |
| 12 | 29.63 | 457.0 | 0.92% | | |
| 13 | 31.06 | 475.1 | 0.48% | | |
| 14 | 27.36 | 421.2 | 0.61% | 5R | 1.21% |
| 15 | 29.78 | 453.1 | 0.41% | | |
| 16 | 30.08 | 455.3 | 0.19% | | |
| 17 | 30.25 | 455.6 | 0.09% | 6R | 0.13% |
| 18 | 29.41 | 441.9 | 0.03% | | |
| 19 | 43.00 | 630.3 | 0.01% | | |
| 20 | | | 0.00% | 7 + R | 0.00% |
| 21 | | | 0.00% | | |

TABLE 9

DBE, weighted average carbon number, weighted average molecular weight, mass fraction per DBE, aromatic ring family and mass fraction of aromatic ring families for N1 class of sample VGO (HCR FEED). Nitrogen is assumed in pyrrole rings.

| DBE | C# | M | Mass Fraction | N1 Aromatic Ring Family | Mass Fraction |
|---|---|---|---|---|---|
| −0.5 | | | 0.000% | SAT | 0.000% |
| 0.5 | | | 0.000% | | |
| 1.5 | | | 0.000% | | |
| 2.5 | | | 0.000% | 1R | 0.000% |
| 3.5 | | | 0.000% | | |
| 4.5 | | | 0.000% | | |
| 5.5 | | | 0.000% | 2R | 0.001% |
| 6.5 | | | 0.000% | | |
| 7.5 | 29.80 | 417.6 | 0.001% | | |
| 8.5 | 27.55 | 384.0 | 0.017% | 3R | 0.063% |
| 9.5 | 27.39 | 379.7 | 0.019% | | |
| 10.5 | 29.82 | 411.8 | 0.027% | | |
| 11.5 | 28.47 | 390.9 | 0.033% | 4R | 0.078% |
| 12.5 | 29.90 | 408.9 | 0.026% | | |
| 13.5 | 30.38 | 413.7 | 0.019% | | |
| 14.5 | 30.03 | 406.7 | 0.014% | 5R | 0.028% |
| 15.5 | 30.78 | 415.1 | 0.010% | | |
| 16.5 | 31.72 | 426.3 | 0.004% | | |
| 17.5 | 33.78 | 453.2 | 0.001% | 6R | 0.001% |
| 18.5 | | | 0.000% | | |
| 19.5 | | | 0.000% | | |
| 20.5 | | | 0.000% | 7 + R | 0.000% |

TABLE 10

DBE, weighted average carbon number, weighted average molecular weight, mass fraction per DBE, aromatic ring family and mass fraction of aromatic ring families for HC class of sample VGO (HCR FEED).

| DBE | C# | M | Mass Fraction | HC Aromatic Ring Family | Mass Fraction |
|---|---|---|---|---|---|
| 0 | | | | SAT | 27.17%[1] |
| 1 | | | | | |
| 2 | | | | | |
| 3 | | | | | |
| 4 | 31.51 | 435.6 | 5.14% | 1R | 14.78% |
| 5 | 32.57 | 448.5 | 5.28% | | |
| 6 | 33.31 | 456.8 | 4.36% | | |
| 7 | 33.20 | 453.3 | 3.82% | 2R | 10.59% |
| 8 | 32.89 | 446.9 | 3.45% | | |
| 9 | 32.46 | 438.9 | 3.31% | | |
| 10 | 32.43 | 436.4 | 2.62% | 3R | 6.71% |
| 11 | 30.97 | 413.9 | 2.15% | | |
| 12 | 29.36 | 389.3 | 1.94% | | |
| 13 | 32.03 | 424.8 | 1.11% | 4R | 2.36% |
| 14 | 32.32 | 426.8 | 0.73% | | |
| 15 | 31.25 | 409.8 | 0.52% | | |
| 16 | 31.94 | 417.4 | 0.36% | 5R | 0.60% |
| 17 | 32.94 | 429.4 | 0.17% | | |
| 18 | 31.98 | 413.9 | 0.06% | | |
| 19 | 33.83 | 437.9 | 0.03% | 6R | 0.04% |
| 20 | 35.39 | 457.7 | 0.01% | | |
| 21 | | | 0.00% | | |

[1] The mass fraction of saturated hydrocarbon compounds is determined separately in step 180.

In step 195, carbon number distributions are calculated for each aromatic ring family. The mass fractions of each DBE series are distributed among its members, based on the individual mass spectral abundances obtained in step 140, to provide the breakdown per carbon number. Carbon number mass fractions of the individual DBE series are then combined according to Table 1 into the aromatic ring families, to calculate their carbon number distributions. For example, the mass fractions for carbon number 20 in DBE series 6, 7, and 8 are summed to obtain the mass fraction of carbon number 20 for the S1-2R family. The results for the S1, S2, N1, and HC class aromatic ring families determined for sample VGO (HCR FEED) are listed in Table 11, 12, 13 and 14, respectively.

TABLE 11

Mass fractions per carbon number (C#) for the S1 class aromatic ring families of sample VGO (HCR FEED).

| C# | S1-1R | S1-2R | S1-3R | S1-4R | S1-5R | S1-6R | S1-7R+ |
|---|---|---|---|---|---|---|---|
| 10 | 0.0000% | 0.0000% | 0.0000% | 0.0000% | 0.0000% | 0.0000% | 0.0000% |
| 11 | 0.0000% | 0.0000% | 0.0000% | 0.0000% | 0.0000% | 0.0000% | 0.0000% |
| 12 | 0.0000% | 0.0000% | 0.0000% | 0.0000% | 0.0000% | 0.0000% | 0.0000% |
| 13 | 0.0000% | 0.0000% | 0.0000% | 0.0000% | 0.0000% | 0.0000% | 0.0000% |
| 14 | 0.0000% | 0.0000% | 0.0000% | 0.0000% | 0.0000% | 0.0000% | 0.0000% |
| 15 | 0.0000% | 0.0000% | 0.0038% | 0.0000% | 0.0000% | 0.0000% | 0.0000% |
| 16 | 0.0000% | 0.0089% | 0.0122% | 0.0000% | 0.0000% | 0.0000% | 0.0000% |
| 17 | 0.0077% | 0.0511% | 0.0506% | 0.0034% | 0.0000% | 0.0000% | 0.0000% |
| 18 | 0.0133% | 0.1106% | 0.1021% | 0.0273% | 0.0000% | 0.0000% | 0.0000% |
| 19 | 0.0260% | 0.1628% | 0.1335% | 0.0501% | 0.0000% | 0.0000% | 0.0000% |
| 20 | 0.0356% | 0.2083% | 0.1508% | 0.0652% | 0.0000% | 0.0000% | 0.0000% |
| 21 | 0.0536% | 0.2246% | 0.1884% | 0.0784% | 0.0033% | 0.0000% | 0.0000% |
| 22 | 0.0639% | 0.4170% | 0.2431% | 0.1014% | 0.0101% | 0.0000% | 0.0000% |
| 23 | 0.0659% | 0.4176% | 0.2399% | 0.1413% | 0.0203% | 0.0000% | 0.0000% |
| 24 | 0.0840% | 0.5621% | 0.2659% | 0.1450% | 0.0312% | 0.0000% | 0.0000% |
| 25 | 0.1236% | 0.6219% | 0.3183% | 0.1631% | 0.0382% | 0.0000% | 0.0000% |
| 26 | 0.0998% | 0.5391% | 0.4514% | 0.1975% | 0.0482% | 0.0024% | 0.0000% |
| 27 | 0.1080% | 0.6520% | 0.4200% | 0.1503% | 0.0644% | 0.0072% | 0.0000% |
| 28 | 0.1218% | 0.5645% | 0.3846% | 0.1833% | 0.0683% | 0.0094% | 0.0000% |
| 29 | 0.1717% | 0.9364% | 0.5247% | 0.1697% | 0.0550% | 0.0074% | 0.0000% |
| 30 | 0.1417% | 0.8243% | 0.5978% | 0.2743% | 0.0835% | 0.0067% | 0.0000% |
| 31 | 0.1502% | 0.7754% | 0.5138% | 0.2314% | 0.0855% | 0.0145% | 0.0000% |
| 32 | 0.1379% | 0.8142% | 0.5509% | 0.2347% | 0.0756% | 0.0153% | 0.0031% |
| 33 | 0.1207% | 0.7294% | 0.5034% | 0.2392% | 0.0809% | 0.0149% | 0.0000% |
| 34 | 0.1245% | 0.6701% | 0.4590% | 0.2173% | 0.0745% | 0.0137% | 0.0000% |
| 35 | 0.1124% | 0.6406% | 0.4290% | 0.1969% | 0.0714% | 0.0062% | 0.0000% |
| 36 | 0.1111% | 0.6056% | 0.4125% | 0.1871% | 0.0705% | 0.0040% | 0.0000% |
| 37 | 0.0972% | 0.5629% | 0.3861% | 0.1818% | 0.0629% | 0.0098% | 0.0000% |
| 38 | 0.0829% | 0.4587% | 0.3308% | 0.1617% | 0.0452% | 0.0107% | 0.0000% |
| 39 | 0.0677% | 0.3756% | 0.2844% | 0.1322% | 0.0470% | 0.0100% | 0.0000% |
| 40 | 0.0625% | 0.3293% | 0.2357% | 0.1084% | 0.0355% | 0.0000% | 0.0000% |
| 41 | 0.0603% | 0.2891% | 0.2069% | 0.0975% | 0.0324% | 0.0000% | 0.0000% |
| 42 | 0.0445% | 0.2624% | 0.1883% | 0.0857% | 0.0231% | 0.0000% | 0.0000% |
| 43 | 0.0472% | 0.2359% | 0.1723% | 0.0860% | 0.0188% | 0.0000% | 0.0000% |
| 44 | 0.0310% | 0.2109% | 0.1592% | 0.0777% | 0.0147% | 0.0000% | 0.0000% |
| 45 | 0.0240% | 0.1648% | 0.1237% | 0.0653% | 0.0158% | 0.0000% | 0.0000% |
| 46 | 0.0181% | 0.1291% | 0.0939% | 0.0438% | 0.0067% | 0.0000% | 0.0000% |
| 47 | 0.0065% | 0.0967% | 0.0757% | 0.0344% | 0.0062% | 0.0000% | 0.0000% |
| 48 | 0.0063% | 0.0689% | 0.0587% | 0.0261% | 0.0000% | 0.0000% | 0.0000% |
| 49 | 0.0000% | 0.0471% | 0.0379% | 0.0087% | 0.0000% | 0.0000% | 0.0000% |
| 50 | 0.0000% | 0.0158% | 0.0283% | 0.0000% | 0.0000% | 0.0000% | 0.0000% |
| 51 | 0.0000% | 0.0166% | 0.0231% | 0.0000% | 0.0000% | 0.0000% | 0.0000% |
| 52 | 0.0000% | 0.0189% | 0.0058% | 0.0000% | 0.0000% | 0.0000% | 0.0000% |
| 53 | 0.0000% | 0.0000% | 0.0000% | 0.0000% | 0.0000% | 0.0000% | 0.0000% |
| 54 | 0.0000% | 0.0000% | 0.0070% | 0.0000% | 0.0000% | 0.0000% | 0.0000% |
| 55 | 0.0000% | 0.0000% | 0.0000% | 0.0000% | 0.0000% | 0.0000% | 0.0000% |

TABLE 12

Mass fractions per carbon number (C#) for the S2 class aromatic ring families of sample VGO (HCR FEED).

| C# | S2-1R | S2-2R | S2-3R | S2-4R | S2-5R | S2-6R |
|---|---|---|---|---|---|---|
| 10 | 0.0000% | 0.0000% | 0.0000% | 0.0000% | 0.0000% | 0.0000% |
| 11 | 0.0000% | 0.0000% | 0.0000% | 0.0000% | 0.0000% | 0.0000% |
| 12 | 0.0000% | 0.0000% | 0.0000% | 0.0000% | 0.0000% | 0.0000% |
| 13 | 0.0000% | 0.0000% | 0.0000% | 0.0000% | 0.0000% | 0.0000% |
| 14 | 0.0000% | 0.0000% | 0.0000% | 0.0000% | 0.0000% | 0.0000% |
| 15 | 0.0000% | 0.0000% | 0.0000% | 0.0000% | 0.0000% | 0.0000% |
| 16 | 0.0000% | 0.0000% | 0.0051% | 0.0070% | 0.0000% | 0.0000% |
| 17 | 0.0000% | 0.0000% | 0.0088% | 0.0199% | 0.0000% | 0.0000% |
| 18 | 0.0000% | 0.0000% | 0.0116% | 0.0368% | 0.0000% | 0.0000% |
| 19 | 0.0000% | 0.0040% | 0.0132% | 0.0554% | 0.0050% | 0.0000% |
| 20 | 0.0000% | 0.0141% | 0.0313% | 0.0709% | 0.0183% | 0.0000% |
| 21 | 0.0049% | 0.0054% | 0.0358% | 0.0705% | 0.0405% | 0.0000% |
| 22 | 0.0000% | 0.0139% | 0.0474% | 0.0821% | 0.0475% | 0.0000% |
| 23 | 0.0000% | 0.0292% | 0.0707% | 0.0997% | 0.0680% | 0.0000% |
| 24 | 0.0000% | 0.0210% | 0.0471% | 0.1485% | 0.0847% | 0.0054% |
| 25 | 0.0075% | 0.0214% | 0.0678% | 0.1409% | 0.0636% | 0.0066% |
| 26 | 0.0084% | 0.0074% | 0.0593% | 0.1215% | 0.0785% | 0.0074% |
| 27 | 0.0065% | 0.0451% | 0.1215% | 0.1666% | 0.0576% | 0.0000% |

TABLE 12-continued

Mass fractions per carbon number (C#) for the S2 class aromatic ring families of sample VGO (HCR FEED).

| C# | S2-1R | S2-2R | S2-3R | S2-4R | S2-5R | S2-6R |
|---|---|---|---|---|---|---|
| 28 | 0.0078% | 0.0378% | 0.1076% | 0.1977% | 0.0986% | 0.0176% |
| 29 | 0.0000% | 0.0275% | 0.1016% | 0.1799% | 0.0904% | 0.0171% |
| 30 | 0.0000% | 0.0192% | 0.1121% | 0.1737% | 0.0856% | 0.0082% |
| 31 | 0.0000% | 0.0157% | 0.0878% | 0.1715% | 0.0803% | 0.0148% |
| 32 | 0.0000% | 0.0240% | 0.1183% | 0.1505% | 0.0812% | 0.0073% |
| 33 | 0.0000% | 0.0287% | 0.0941% | 0.1356% | 0.0580% | 0.0069% |
| 34 | 0.0000% | 0.0310% | 0.0922% | 0.1395% | 0.0642% | 0.0105% |
| 35 | 0.0000% | 0.0121% | 0.0938% | 0.1037% | 0.0548% | 0.0098% |
| 36 | 0.0000% | 0.0129% | 0.0720% | 0.0949% | 0.0459% | 0.0088% |
| 37 | 0.0000% | 0.0000% | 0.0418% | 0.0768% | 0.0393% | 0.0000% |
| 38 | 0.0000% | 0.0101% | 0.0559% | 0.0493% | 0.0107% | 0.0000% |
| 39 | 0.0000% | 0.0090% | 0.0386% | 0.0537% | 0.0300% | 0.0000% |
| 40 | 0.0000% | 0.0000% | 0.0211% | 0.0413% | 0.0100% | 0.0000% |
| 41 | 0.0000% | 0.0000% | 0.0450% | 0.0521% | 0.0245% | 0.0000% |
| 42 | 0.0000% | 0.0000% | 0.0254% | 0.0365% | 0.0000% | 0.0000% |
| 43 | 0.0000% | 0.0000% | 0.0091% | 0.0252% | 0.0000% | 0.0066% |
| 44 | 0.0000% | 0.0000% | 0.0198% | 0.0206% | 0.0000% | 0.0000% |
| 45 | 0.0000% | 0.0000% | 0.0000% | 0.0000% | 0.0000% | 0.0000% |

TABLE 13

Mass fractions per carbon number (C#) for the N1 class aromatic ring families of sample VGO (HCR FEED).

| C# | N1-3R | N1-4R | N1-5R | N1-6R |
|---|---|---|---|---|
| 10 | 0.0000% | 0.0000% | 0.0000% | 0.0000% |
| 11 | 0.0000% | 0.0000% | 0.0000% | 0.0000% |
| 12 | 0.0000% | 0.0000% | 0.0000% | 0.0000% |
| 13 | 0.0000% | 0.0000% | 0.0000% | 0.0000% |
| 14 | 0.0000% | 0.0000% | 0.0000% | 0.0000% |
| 15 | 0.0000% | 0.0000% | 0.0000% | 0.0000% |
| 16 | 0.0000% | 0.0000% | 0.0000% | 0.0000% |
| 17 | 0.0000% | 0.0000% | 0.0000% | 0.0000% |
| 18 | 0.0007% | 0.0000% | 0.0000% | 0.0000% |
| 19 | 0.0009% | 0.0005% | 0.0000% | 0.0000% |
| 20 | 0.0014% | 0.0021% | 0.0000% | 0.0000% |
| 21 | 0.0012% | 0.0026% | 0.0000% | 0.0000% |
| 22 | 0.0015% | 0.0023% | 0.0000% | 0.0000% |
| 23 | 0.0019% | 0.0034% | 0.0008% | 0.0000% |
| 24 | 0.0021% | 0.0045% | 0.0012% | 0.0000% |
| 25 | 0.0018% | 0.0040% | 0.0018% | 0.0000% |
| 26 | 0.0019% | 0.0047% | 0.0021% | 0.0000% |
| 27 | 0.0028% | 0.0048% | 0.0033% | 0.0000% |
| 28 | 0.0027% | 0.0046% | 0.0036% | 0.0000% |
| 29 | 0.0019% | 0.0040% | 0.0035% | 0.0004% |
| 30 | 0.0027% | 0.0042% | 0.0027% | 0.0004% |
| 31 | 0.0025% | 0.0065% | 0.0040% | 0.0006% |
| 32 | 0.0030% | 0.0051% | 0.0039% | 0.0012% |
| 33 | 0.0024% | 0.0047% | 0.0035% | 0.0007% |
| 34 | 0.0023% | 0.0054% | 0.0043% | 0.0007% |
| 35 | 0.0017% | 0.0043% | 0.0021% | 0.0007% |
| 36 | 0.0017% | 0.0050% | 0.0026% | 0.0000% |
| 37 | 0.0016% | 0.0038% | 0.0018% | 0.0000% |
| 38 | 0.0000% | 0.0030% | 0.0000% | 0.0000% |
| 39 | 0.0000% | 0.0033% | 0.0000% | 0.0000% |
| 40 | 0.0000% | 0.0026% | 0.0007% | 0.0000% |
| 41 | 0.0000% | 0.0007% | 0.0000% | 0.0000% |
| 42 | 0.0000% | 0.0000% | 0.0000% | 0.0000% |

TABLE 14

Mass fractions per carbon number (C#) for the HC class aromatic ring families of sample VGO (HCR FEED).

| C# | HC-1R | HC-2R | HC-3R | HC-4R | HC-5R | HC-6R+ |
|---|---|---|---|---|---|---|
| 10 | 0.0000% | 0.0000% | 0.0000% | 0.0000% | 0.0000% | 0.0000% |
| 11 | 0.0000% | 0.0000% | 0.0000% | 0.0000% | 0.0000% | 0.0000% |
| 12 | 0.0000% | 0.0000% | 0.0000% | 0.0000% | 0.0000% | 0.0000% |
| 13 | 0.0000% | 0.0000% | 0.0000% | 0.0000% | 0.0000% | 0.0000% |
| 14 | 0.0000% | 0.0000% | 0.0000% | 0.0000% | 0.0000% | 0.0000% |
| 15 | 0.0014% | 0.0000% | 0.0000% | 0.0000% | 0.0000% | 0.0000% |
| 16 | 0.0012% | 0.0000% | 0.0000% | 0.0000% | 0.0000% | 0.0000% |
| 17 | 0.0014% | 0.0000% | 0.0000% | 0.0000% | 0.0000% | 0.0000% |
| 18 | 0.0030% | 0.0083% | 0.0051% | 0.0000% | 0.0000% | 0.0000% |
| 19 | 0.0290% | 0.0411% | 0.0257% | 0.0000% | 0.0000% | 0.0000% |
| 20 | 0.0816% | 0.0850% | 0.0920% | 0.0071% | 0.0000% | 0.0000% |
| 21 | 0.1454% | 0.1278% | 0.3991% | 0.0257% | 0.0000% | 0.0000% |
| 22 | 0.1884% | 0.1728% | 0.2328% | 0.0343% | 0.0016% | 0.0000% |
| 23 | 0.2376% | 0.1809% | 0.1377% | 0.0395% | 0.0000% | 0.0000% |
| 24 | 0.4116% | 0.2493% | 0.1418% | 0.0583% | 0.0025% | 0.0000% |
| 25 | 0.4720% | 0.2503% | 0.1999% | 0.0768% | 0.0105% | 0.0000% |
| 26 | 0.5605% | 0.2865% | 0.2261% | 0.0953% | 0.0173% | 0.0000% |
| 27 | 0.6839% | 0.4070% | 0.2767% | 0.0978% | 0.0240% | 0.0000% |
| 28 | 0.6380% | 0.5669% | 0.3447% | 0.1754% | 0.0630% | 0.0000% |
| 29 | 0.8271% | 0.5198% | 0.2631% | 0.1378% | 0.0670% | 0.0000% |

TABLE 14-continued

Mass fractions per carbon number (C#) for the HC class aromatic ring families of sample VGO (HCR FEED).

| C# | HC-1R | HC-2R | HC-3R | HC-4R | HC-5R | HC-6R+ |
|---|---|---|---|---|---|---|
| 30 | 0.6965% | 0.4306% | 0.2900% | 0.1278% | 0.0336% | 0.0000% |
| 31 | 1.0529% | 0.5485% | 0.2633% | 0.1020% | 0.0345% | 0.0032% |
| 32 | 0.9219% | 0.6311% | 0.4112% | 0.1499% | 0.0353% | 0.0030% |
| 33 | 0.8214% | 0.5524% | 0.3434% | 0.1448% | 0.0507% | 0.0058% |
| 34 | 0.8414% | 0.5822% | 0.3355% | 0.1310% | 0.0375% | 0.0057% |
| 35 | 0.7292% | 0.5393% | 0.3236% | 0.1397% | 0.0491% | 0.0138% |
| 36 | 0.6562% | 0.4778% | 0.2842% | 0.1211% | 0.0380% | 0.0090% |
| 37 | 0.6053% | 0.4590% | 0.2721% | 0.1062% | 0.0294% | 0.0000% |
| 38 | 0.5947% | 0.4459% | 0.2650% | 0.1071% | 0.0250% | 0.0000% |
| 39 | 0.5501% | 0.4313% | 0.2521% | 0.0988% | 0.0127% | 0.0000% |
| 40 | 0.4774% | 0.3922% | 0.2326% | 0.0835% | 0.0204% | 0.0000% |
| 41 | 0.3814% | 0.3148% | 0.1887% | 0.0774% | 0.0162% | 0.0000% |
| 42 | 0.3315% | 0.2808% | 0.1566% | 0.0487% | 0.0136% | 0.0000% |
| 43 | 0.3064% | 0.2481% | 0.1261% | 0.0436% | 0.0088% | 0.0000% |
| 44 | 0.2868% | 0.2348% | 0.1189% | 0.0380% | 0.0000% | 0.0000% |
| 45 | 0.2608% | 0.2233% | 0.1046% | 0.0382% | 0.0000% | 0.0000% |
| 46 | 0.2392% | 0.1943% | 0.1079% | 0.0266% | 0.0058% | 0.0000% |
| 47 | 0.1921% | 0.1694% | 0.0932% | 0.0212% | 0.0000% | 0.0000% |
| 48 | 0.1509% | 0.1401% | 0.0620% | 0.0079% | 0.0000% | 0.0000% |
| 49 | 0.1162% | 0.1093% | 0.0459% | 0.0000% | 0.0000% | 0.0000% |
| 50 | 0.0831% | 0.0834% | 0.0408% | 0.0000% | 0.0000% | 0.0000% |
| 51 | 0.0653% | 0.0633% | 0.0225% | 0.0000% | 0.0000% | 0.0000% |
| 52 | 0.0514% | 0.0498% | 0.0086% | 0.0000% | 0.0000% | 0.0000% |
| 53 | 0.0395% | 0.0406% | 0.0068% | 0.0000% | 0.0000% | 0.0000% |
| 54 | 0.0155% | 0.0247% | 0.0063% | 0.0000% | 0.0000% | 0.0000% |
| 55 | 0.0184% | 0.0065% | 0.0000% | 0.0000% | 0.0000% | 0.0000% |
| 56 | 0.0132% | 0.0092% | 0.0000% | 0.0000% | 0.0000% | 0.0000% |
| 57 | 0.0000% | 0.0000% | 0.0000% | 0.0000% | 0.0000% | 0.0000% |
| 58 | 0.0000% | 0.0069% | 0.0000% | 0.0000% | 0.0000% | 0.0000% |
| 59 | 0.0000% | 0.0000% | 0.0000% | 0.0000% | 0.0000% | 0.0000% |
| 60 | 0.0000% | 0.0000% | 0.0000% | 0.0000% | 0.0000% | 0.0000% |

In step 200, the total alkyl chain length for each aromatic ring family are calculated. The number of carbon atoms contained in aromatic rings, listed in Table 2 for typical heteroatom classes, are subtracted from the carbon numbers derived in step 195 (see Tables 11-14). The results for sample VGO (HCR FEED) are listed in Table1 15-18.

TABLE 15

Mass fractions per total alkyl chain length ($C_{Alk.}$) for the S1 class aromatic ring families of sample VGO (HCR FEED).

| C(Alk.) | S1-1R | S1-2R | S1-3R | S1-4R | S1-5R | S1-6R | S1-7R+ |
|---|---|---|---|---|---|---|---|
| 0 | 0.0000% | 0.0000% | 0.0000% | 0.0000% | 0.0000% | 0.0000% | 0.0000% |
| 1 | 0.0000% | 0.0000% | 0.0000% | 0.0035% | 0.0033% | 0.0000% | 0.0000% |
| 2 | 0.0000% | 0.0000% | 0.0000% | 0.0280% | 0.0100% | 0.0023% | 0.0000% |
| 3 | 0.0000% | 0.0000% | 0.0039% | 0.0514% | 0.0199% | 0.0070% | 0.0000% |
| 4 | 0.0000% | 0.0000% | 0.0126% | 0.0665% | 0.0307% | 0.0092% | 0.0032% |
| 5 | 0.0000% | 0.0000% | 0.0514% | 0.0795% | 0.0375% | 0.0073% | |
| 6 | 0.0000% | 0.0000% | 0.1033% | 0.1027% | 0.0473% | 0.0066% | |
| 7 | 0.0000% | 0.0000% | 0.1348% | 0.1426% | 0.0632% | 0.0142% | |
| 8 | 0.0000% | 0.0090% | 0.1519% | 0.1462% | 0.0670% | 0.0150% | |
| 9 | 0.0000% | 0.0516% | 0.1902% | 0.1645% | 0.0539% | 0.0145% | |
| 10 | 0.0000% | 0.1113% | 0.2446% | 0.1997% | 0.0820% | 0.0134% | |
| 11 | 0.0000% | 0.1636% | 0.2414% | 0.1517% | 0.0839% | 0.0061% | |
| 12 | 0.0000% | 0.2096% | 0.2677% | 0.1850% | 0.0742% | 0.0040% | |
| 13 | 0.0076% | 0.2251% | 0.3203% | 0.1716% | 0.0795% | 0.0095% | |
| 14 | 0.0132% | 0.4199% | 0.4536% | 0.2771% | 0.0732% | 0.0104% | |
| 15 | 0.0257% | 0.4180% | 0.4231% | 0.2337% | 0.0701% | 0.0097% | |
| 16 | 0.0352% | 0.5642% | 0.3865% | 0.2371% | 0.0692% | | |
| 17 | 0.0529% | 0.6251% | 0.5284% | 0.2415% | 0.0617% | | |
| 18 | 0.0630% | 0.5388% | 0.6005% | 0.2196% | 0.0444% | | |
| 19 | 0.0652% | 0.6514% | 0.5162% | 0.1989% | 0.0462% | | |
| 20 | 0.0830% | 0.5643% | 0.5532% | 0.1890% | 0.0349% | | |
| 21 | 0.1221% | 0.9347% | 0.5051% | 0.1836% | 0.0317% | | |
| 22 | 0.0985% | 0.8214% | 0.4605% | 0.1633% | 0.0226% | | |
| 23 | 0.1066% | 0.7725% | 0.4304% | 0.1334% | 0.0185% | | |
| 24 | 0.1202% | 0.8100% | 0.4138% | 0.1095% | 0.0144% | | |
| 25 | 0.1694% | 0.7248% | 0.3871% | 0.0984% | 0.0155% | | |
| 26 | 0.1398% | 0.6654% | 0.3315% | 0.0866% | 0.0066% | | |
| 27 | 0.1482% | 0.6354% | 0.2851% | 0.0869% | 0.0061% | | |
| 28 | 0.1361% | 0.6005% | 0.2361% | 0.0786% | | | |

TABLE 15-continued

Mass fractions per total alkyl chain length ($C_{Alk.}$) for the S1 class aromatic ring families of sample VGO (HCR FEED).

| C(Alk.) | S1-1R | S1-2R | S1-3R | S1-4R | S1-5R | S1-6R | S1-7R+ |
|---|---|---|---|---|---|---|---|
| 29 | 0.1190% | 0.5575% | 0.2074% | 0.0660% | | | |
| 30 | 0.1228% | 0.4540% | 0.1887% | 0.0441% | | | |
| 31 | 0.1108% | 0.3713% | 0.1727% | 0.0348% | | | |
| 32 | 0.1096% | 0.3254% | 0.1596% | 0.0264% | | | |
| 33 | 0.0958% | 0.2856% | 0.1239% | 0.0090% | | | |
| 34 | 0.0817% | 0.2589% | 0.0941% | | | | |
| 35 | 0.0667% | 0.2325% | 0.0758% | | | | |
| 36 | 0.0618% | 0.2075% | 0.0587% | | | | |
| 37 | 0.0595% | 0.1623% | 0.0380% | | | | |
| 38 | 0.0439% | 0.1269% | 0.0284% | | | | |
| 39 | 0.0466% | 0.0951% | 0.0232% | | | | |
| 40 | 0.0304% | 0.0677% | 0.0057% | | | | |
| 41 | 0.0236% | 0.0463% | | | | | |
| 42 | 0.0178% | 0.0152% | | | | | |
| 43 | 0.0065% | 0.0162% | | | | | |
| 44 | 0.0062% | 0.0186% | | | | | |

TABLE 16

Mass fractions per total alkyl chain length ($C_{Alk.}$) for the S2 class aromatic ring families of sample VGO (HCR FEED).

| C(Alk.) | S2-1R | S2-2R | S2-3R | S2-4R | S2-5R | S2-6R |
|---|---|---|---|---|---|---|
| 0 | 0.0000% | 0.0000% | 0.0000% | 0.0000% | 0.0000% | 0.0000% |
| 1 | 0.0000% | 0.0000% | 0.0000% | 0.0000% | 0.0050% | 0.0000% |
| 2 | 0.0000% | 0.0000% | 0.0000% | 0.0070% | 0.0183% | 0.0054% |
| 3 | 0.0000% | 0.0000% | 0.0000% | 0.0199% | 0.0405% | 0.0066% |
| 4 | 0.0000% | 0.0000% | 0.0000% | 0.0368% | 0.0475% | 0.0074% |
| 5 | 0.0000% | 0.0000% | 0.0000% | 0.0554% | 0.0680% | 0.0000% |
| 6 | 0.0000% | 0.0000% | 0.0051% | 0.0709% | 0.0847% | 0.0176% |
| 7 | 0.0000% | 0.0000% | 0.0088% | 0.0705% | 0.0636% | 0.0171% |
| 8 | 0.0000% | 0.0000% | 0.0116% | 0.0821% | 0.0785% | 0.0082% |
| 9 | 0.0000% | 0.0000% | 0.0132% | 0.0997% | 0.0576% | 0.0148% |
| 10 | 0.0000% | 0.0000% | 0.0313% | 0.1485% | 0.0986% | 0.0073% |
| 11 | 0.0000% | 0.0000% | 0.0358% | 0.1409% | 0.0904% | 0.0069% |
| 12 | 0.0000% | 0.0000% | 0.0474% | 0.1215% | 0.0856% | 0.0105% |
| 13 | 0.0000% | 0.0040% | 0.0707% | 0.1666% | 0.0803% | 0.0098% |
| 14 | 0.0000% | 0.0141% | 0.0471% | 0.1977% | 0.0812% | 0.0088% |
| 15 | 0.0000% | 0.0054% | 0.0678% | 0.1799% | 0.0580% | |
| 16 | 0.0000% | 0.0139% | 0.0593% | 0.1737% | 0.0642% | |
| 17 | 0.0049% | 0.0292% | 0.1215% | 0.1715% | 0.0548% | |
| 18 | 0.0000% | 0.0210% | 0.1076% | 0.1505% | 0.0459% | |
| 19 | 0.0000% | 0.0214% | 0.1016% | 0.1356% | 0.0393% | |
| 20 | 0.0000% | 0.0074% | 0.1121% | 0.1395% | 0.0107% | |
| 21 | 0.0075% | 0.0451% | 0.0878% | 0.1037% | 0.0300% | |
| 22 | 0.0084% | 0.0378% | 0.1183% | 0.0949% | 0.0100% | |
| 23 | 0.0065% | 0.0275% | 0.0941% | 0.0768% | 0.0245% | |
| 24 | 0.0078% | 0.0192% | 0.0922% | 0.0493% | | |
| 25 | | 0.0157% | 0.0938% | 0.0537% | | |
| 26 | | 0.0240% | 0.0720% | 0.0413% | | |
| 27 | | 0.0287% | 0.0418% | 0.0521% | | |
| 28 | | 0.0310% | 0.0559% | 0.0365% | | |
| 29 | | 0.0121% | 0.0386% | 0.0252% | | |
| 30 | | 0.0129% | 0.0211% | 0.0206% | | |
| 31 | | 0.0000% | 0.0450% | | | |
| 32 | | 0.0101% | 0.0254% | | | |
| 33 | | 0.0090% | 0.0091% | | | |
| 34 | | | 0.0198% | | | |

TABLE 17

Mass fractions per total alkyl chain length ($C_{Alk.}$) for the N1 class aromatic ring families of sample VGO (HCR FEED).

| C(Alk.) | N1-3R | N1-4R | N1-5R |
|---|---|---|---|
| 0 | 0.0000% | 0.0000% | 0.0000% |
| 1 | 0.0000% | 0.0000% | 0.0000% |
| 2 | 0.0000% | 0.0000% | 0.0000% |
| 3 | 0.0000% | 0.0005% | 0.0008% |
| 4 | 0.0000% | 0.0021% | 0.0012% |
| 5 | 0.0000% | 0.0026% | 0.0018% |

TABLE 17-continued

Mass fractions per total alkyl chain length ($C_{Alk.}$) for the N1 class aromatic ring families of sample VGO (HCR FEED).

| C(Alk.) | N1-3R | N1-4R | N1-5R |
|---|---|---|---|
| 6 | 0.0007% | 0.0023% | 0.0021% |
| 7 | 0.0009% | 0.0034% | 0.0033% |
| 8 | 0.0014% | 0.0045% | 0.0036% |
| 9 | 0.0012% | 0.0040% | 0.0035% |
| 10 | 0.0015% | 0.0047% | 0.0027% |
| 11 | 0.0019% | 0.0048% | 0.0040% |
| 12 | 0.0021% | 0.0046% | 0.0039% |
| 13 | 0.0018% | 0.0040% | 0.0035% |
| 14 | 0.0019% | 0.0042% | 0.0043% |
| 15 | 0.0028% | 0.0065% | 0.0021% |
| 16 | 0.0027% | 0.0051% | 0.0026% |
| 17 | 0.0019% | 0.0047% | 0.0018% |
| 18 | 0.0027% | 0.0054% | 0.0000% |
| 19 | 0.0025% | 0.0043% | 0.0000% |
| 20 | 0.0030% | 0.0050% | 0.0007% |
| 21 | 0.0024% | 0.0038% | |
| 22 | 0.0023% | 0.0030% | |
| 23 | 0.0017% | 0.0033% | |
| 24 | 0.0017% | 0.0026% | |
| 25 | 0.0016% | 0.0007% | |

TABLE 18

Mass fractions per total alkyl chain length ($C_{Alk.}$) for the HC class aromatic ring families of sample VGO (HCR FEED).

| C(Alk.) | HC-1R | HC-2R | HC-3R | HC-4R | HC-5R | HC-6R+ |
|---|---|---|---|---|---|---|
| 0 | 0.0000% | 0.0000% | 0.0000% | 0.0000% | 0.0016% | 0.0000% |
| 1 | 0.0000% | 0.0000% | 0.0000% | 0.0000% | 0.0000% | 0.0000% |
| 2 | 0.0000% | 0.0000% | 0.0000% | 0.0071% | 0.0025% | 0.0000% |
| 3 | 0.0000% | 0.0000% | 0.0000% | 0.0257% | 0.0105% | 0.0000% |
| 4 | 0.0000% | 0.0000% | 0.0051% | 0.0343% | 0.0173% | 0.0000% |
| 5 | 0.0000% | 0.0000% | 0.0257% | 0.0395% | 0.0240% | 0.0032% |
| 6 | 0.0000% | 0.0000% | 0.0920% | 0.0583% | 0.0630% | 0.0030% |
| 7 | 0.0000% | 0.0000% | 0.3991% | 0.0768% | 0.0670% | 0.0058% |
| 8 | 0.0000% | 0.0083% | 0.2328% | 0.0953% | 0.0336% | 0.0057% |
| 9 | 0.0014% | 0.0411% | 0.1377% | 0.0978% | 0.0345% | 0.0138% |
| 10 | 0.0012% | 0.0850% | 0.1418% | 0.1754% | 0.0353% | 0.0090% |
| 11 | 0.0014% | 0.1278% | 0.1999% | 0.1378% | 0.0507% | |
| 12 | 0.0030% | 0.1728% | 0.2261% | 0.1278% | 0.0375% | |
| 13 | 0.0290% | 0.1809% | 0.2767% | 0.1020% | 0.0491% | |
| 14 | 0.0816% | 0.2493% | 0.3447% | 0.1499% | 0.0380% | |
| 15 | 0.1454% | 0.2503% | 0.2631% | 0.1448% | 0.0294% | |
| 16 | 0.1884% | 0.2865% | 0.2900% | 0.1310% | 0.0250% | |
| 17 | 0.2376% | 0.4070% | 0.2633% | 0.1397% | 0.0127% | |
| 18 | 0.4116% | 0.5669% | 0.4112% | 0.1211% | 0.0204% | |
| 19 | 0.4720% | 0.5198% | 0.3434% | 0.1062% | 0.0162% | |
| 20 | 0.5605% | 0.4306% | 0.3355% | 0.1071% | 0.0136% | |
| 21 | 0.6839% | 0.5485% | 0.3236% | 0.0988% | 0.0088% | |
| 22 | 0.6380% | 0.6311% | 0.2842% | 0.0835% | | |
| 23 | 0.8271% | 0.5524% | 0.2721% | 0.0774% | | |
| 24 | 0.6965% | 0.5822% | 0.2650% | 0.0487% | | |
| 25 | 1.0529% | 0.5393% | 0.2521% | 0.0436% | | |
| 26 | 0.9219% | 0.4778% | 0.2326% | 0.0380% | | |
| 27 | 0.8214% | 0.4590% | 0.1887% | 0.0382% | | |
| 28 | 0.8414% | 0.4459% | 0.1566% | 0.0266% | | |
| 29 | 0.7292% | 0.4313% | 0.1261% | 0.0212% | | |
| 30 | 0.6562% | 0.3922% | 0.1189% | 0.0079% | | |
| 31 | 0.6053% | 0.3148% | 0.1046% | | | |
| 32 | 0.5947% | 0.2808% | 0.1079% | | | |
| 33 | 0.5501% | 0.2481% | 0.0932% | | | |
| 34 | 0.4774% | 0.2348% | 0.0620% | | | |
| 35 | 0.3814% | 0.2233% | 0.0459% | | | |
| 36 | 0.3315% | 0.1943% | 0.0408% | | | |
| 37 | 0.3064% | 0.1694% | 0.0225% | | | |
| 38 | 0.2868% | 0.1401% | 0.0086% | | | |
| 39 | 0.2608% | 0.1093% | 0.0068% | | | |
| 40 | 0.2392% | 0.0834% | 0.0063% | | | |
| 41 | 0.1921% | 0.0633% | | | | |
| 42 | 0.1509% | 0.0498% | | | | |
| 43 | 0.1162% | 0.0406% | | | | |
| 44 | 0.0831% | 0.0247% | | | | |
| 45 | 0.0653% | 0.0065% | | | | |
| 46 | 0.0514% | 0.0092% | | | | |
| 47 | 0.0395% | | | | | |
| 48 | 0.0155% | | | | | |
| 49 | 0.0184% | | | | | |
| 50 | 0.0132% | | | | | |

Figure 4:
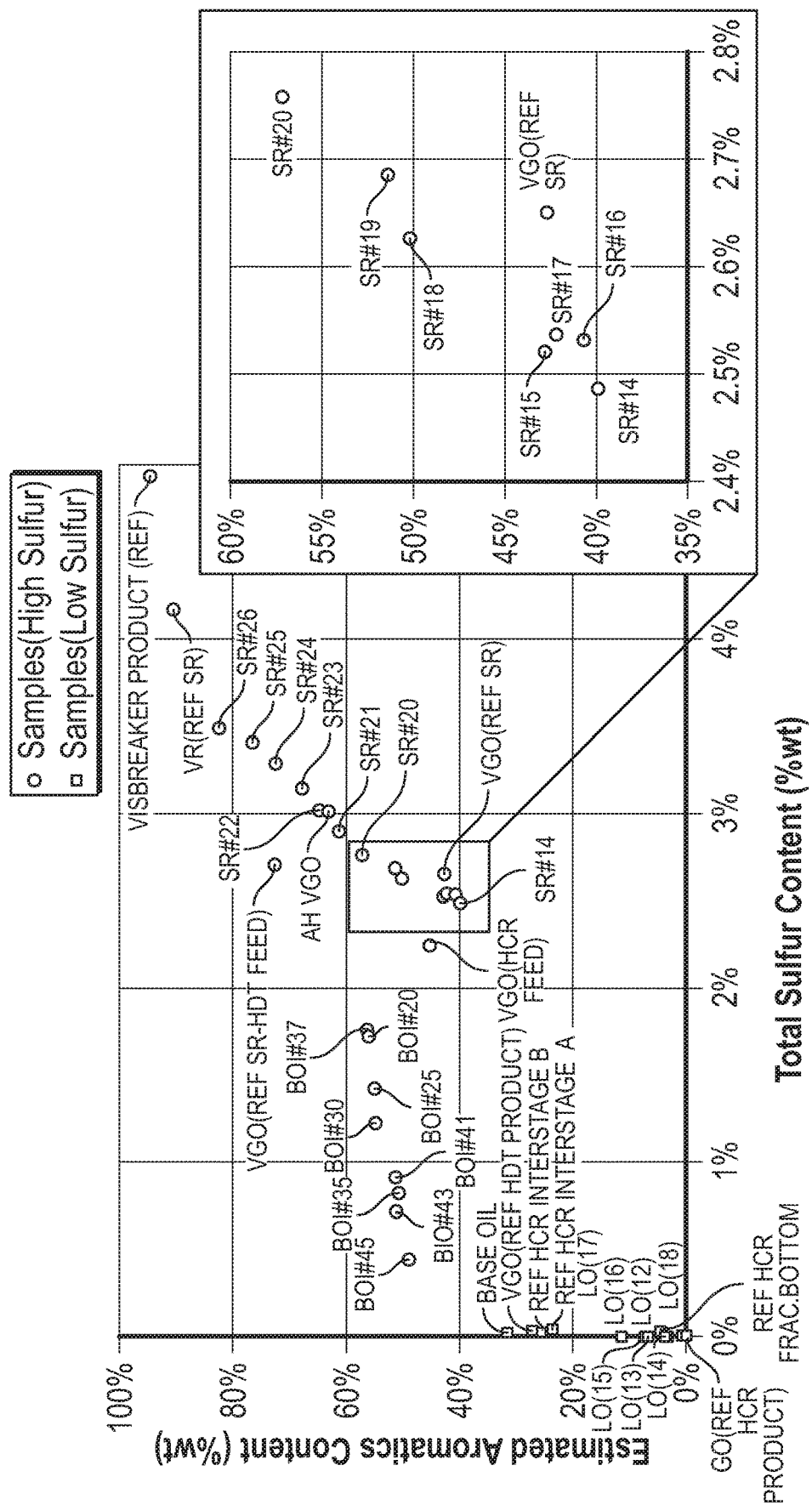
FIG. 4 shows compositions of test samples characterized by an embodiment.

FIG. 4 shows an overview for compositions of test samples characterized by an embodiment of the present disclosure, where the x-axis accounts for the total sulfur content of the samples measured in mass fraction of sulfur. The y-axis accounts for the aromatics content which is the summed mass fraction of all aromatic compounds, including pure hydrocarbon aromatic compounds and sulfur- and nitrogen-containing aromatic compounds. The aliphatics content accounts for the remaining mass fraction. More than 40 example compositions were determined by applying the method described in this invention.

The examples span a wide compositional range including:
total sulfur content from ultra-trace (100 ppm) to very sour >5.5% wt,
aromatic contents from <1% wt to >95% wt,
boiling ranges from middle distillates (initial boiling point, IBP, <260° C.) to vacuum residues with atmospheric equivalent boiling range >560° C., and aliphatic contents from <5% wt to >99% wt.

The aliphatics content is the inverse of the aromatics content. For example, in FIG. 4, sample "VGO (HCR FEED)," a high-boiling hydrocracking unit feedstock has an aromatics content estimated by an embodiment of this method to be 72.8%, and correspondingly contains 27.2% aliphatics (SAT), see the example in Table 6.

Figure 5:
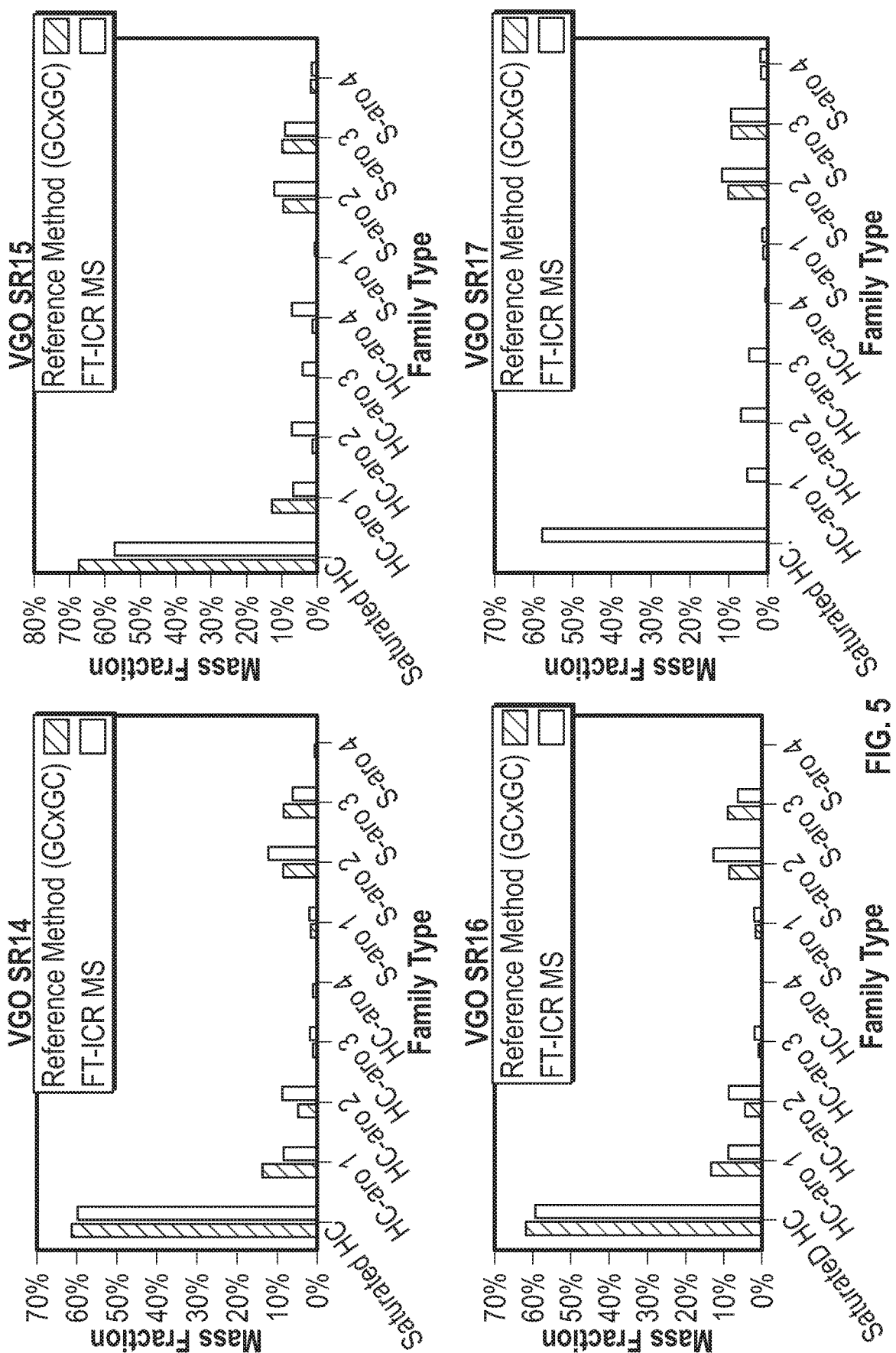
FIG. 5 shows validation data of an embodiment of the invention in comparison to a reference.

FIG. 5 is an example showing validation data for an embodiment of the method in comparison to a reference method employing two-dimensional comprehensive gas chromatography (GC×GC) with four straight run vacuum gas oil samples (VGO SR14-17) of progressively higher boiling point ranges. Hydrocarbon species in the highest boiling sample VGO SR17 could not be successfully separated using the GC×GC method, therefore, only sulfur speciation can be included for this sample.

Figure 6:
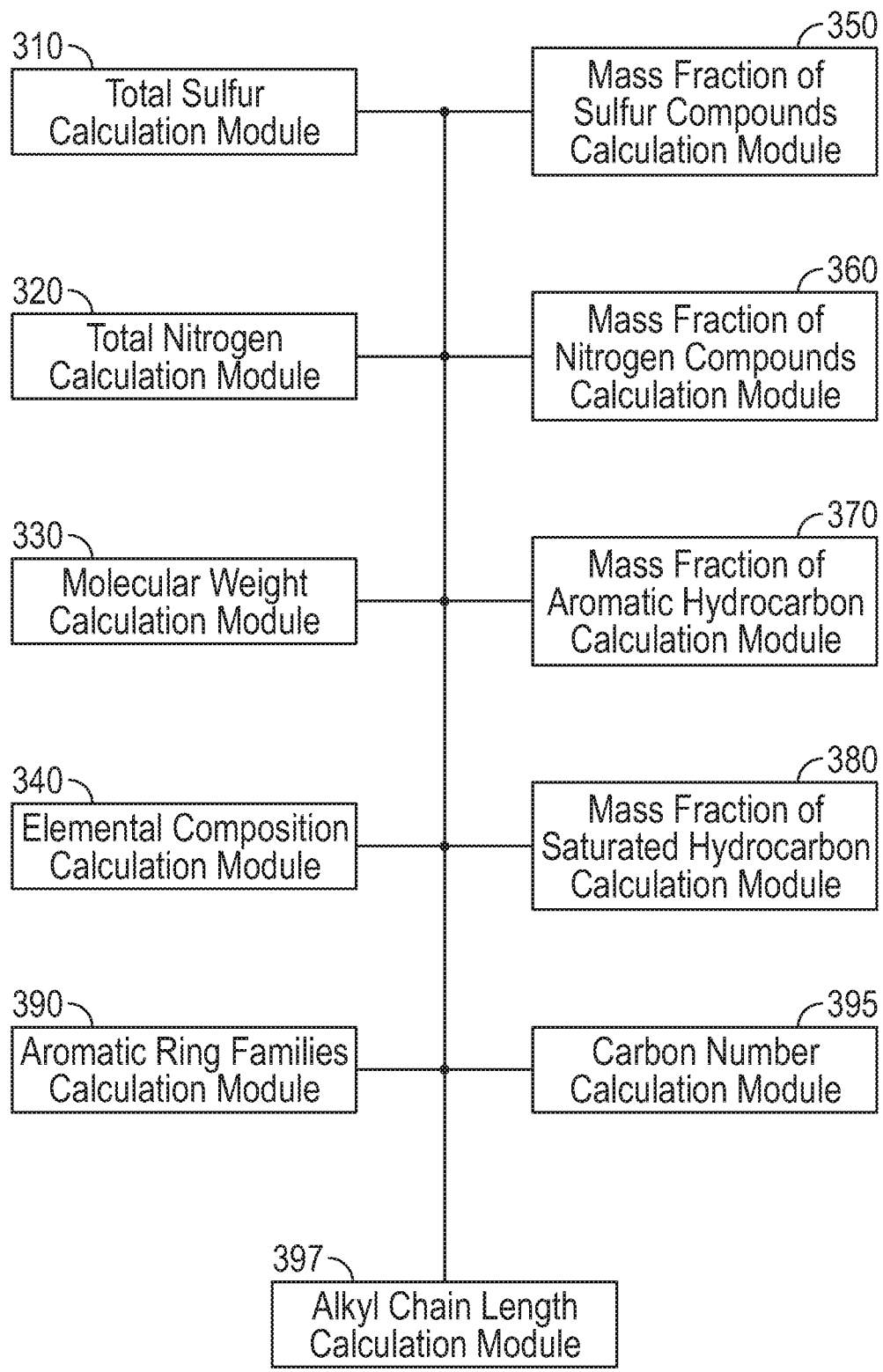
FIG. 6 is a schematic block diagram of modules of an embodiment of the invention.

FIG. 6 shows several computer program calculation modules utilized in the invention. Each of the computer program calculation modules is stored in non-volatile memory in a computer system, and when executed by a processor of the computer system, performs the following calculations, with results being transferred and stored into the non-volatile memory.

Computer program calculation module 310 calculates the total sulfur of a petroleum sample from data from XRF spectroscopy or from another method, as described above with regard to step 110 of method 100.

Computer program calculation module 320 calculates the total nitrogen of the petroleum sample from the oxidative combustion of the sample followed by chemiluminescence detection, as described above with regard to step 120 of method 100.

Computer program calculation module 330 calculates the molecular weight of the petroleum sample from APPI TOF MS data, as described above with regard to step 130 of method 100.

Computer program calculation module 340 calculates the elemental composition of the petroleum sample from APPI FT-ICR MS data, as described above with regard to step 140 of method 100.

Computer program calculation module 350 calculates the mass fraction of sulfur compounds of the petroleum sample, as described above with regard to step 150 of method 100.

Computer program calculation module 360 calculates the mass fraction of nitrogen compounds of the petroleum sample, as described above with regard to step 160 of method 100.

Computer program calculation module 370 calculates the mass fraction of aromatic hydrocarbon of the petroleum sample, as described above with regard to step 170 of method 100. Computer program calculation module 380 calculates the mass fraction of saturated hydrocarbon of the petroleum sample, as described above with regard to step 180 of method 100.

Computer program calculation module 390 calculates aromatic ring number families of the petroleum sample, as described above with regard to step 190 of method 100.

Computer program calculation module 395 calculates carbon number for each aromatic ring number family, as described above with regard to step 195 of method 100.

Computer program calculation module 397 calculates carbon number for each aromatic ring number family, as described above with regard to step 200 of method 100.

It will be understood by one of ordinary skill in the art that these computer program calculation modules can be combined into a fewer number of calculation modules or, alternatively, that one or more of these computer program calculation modules can be split into two or more submodules.

Figure 7:
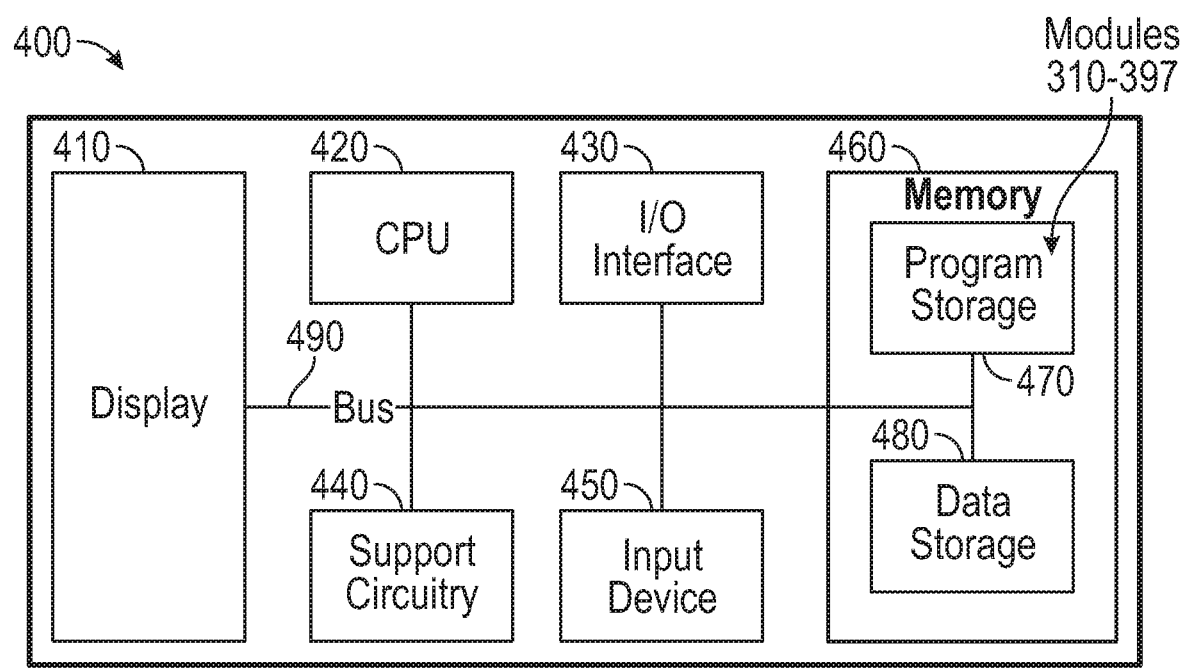
FIG. 7 is a schematic block diagram of a computer system in which an embodiment of the invention is implemented.

FIG. 7 shows an exemplary block diagram of a computer system 400 in which one embodiment of the method of the present disclosure can be implemented. Computer system 400 includes a processor 420, such as a central processing unit (CPU), an input/output interface 430 and support circuitry 440. In certain embodiments, in which the computer system 400 requires a direct human interface, a display 410 and an input device 450 such as a keyboard, mouse or pointer are also provided. The display 410, input device 450, processor 420, and support circuitry 440 are shown connected to a bus 490 which also connects to a memory 460. Memory 460 includes program storage memory 470 and data storage memory 480. Note that while computer system 400 is depicted with direct human interface components display 410 and input device 450, programming of modules and exportation of data can alternatively be accomplished over the input/output interface 430, for instance, where the computer system 400 is connected to a network and the programming and display operations occur on another associated computer, or via a detachable input device as is known with respect to interfacing programmable logic controllers.

Program storage memory 470 and data storage memory 480 can each comprise volatile (RAM) and non-volatile (ROM) memory units and can also comprise hard disk and backup storage capacity, and both program storage memory 470 and data storage memory 480 can be embodied in a single memory device or separated in plural memory devices. Program storage memory 470 stores computer program calculation modules and associated data, and in particular stores computer program calculation module 310, e.g., to calculate the total sulfur of a petroleum sample from XRF spectroscopy data, computer program calculation module 320, e.g., to calculate the total nitrogen of the petroleum sample from oxidative combustion followed by chemiluminescence detection, computer program calculation module 330, e.g., to calculate the molecular weight of the petroleum sample from APPI TOF MS data, computer program calculation module 340, e.g., to calculate the elemental composition of the petroleum sample from APPI FT-ICR MS data, computer program calculation module 350, e.g., to calculate the mass fraction of sulfur compounds of the petroleum sample, computer program calculation module 360, e.g., to calculate the mass fraction of nitrogen compounds of the petroleum sample, computer program calculation module 370, e.g., to calculate the mass fraction of aromatic hydrocarbon of the petroleum sample, computer program calculation module 380, e.g., to calculate the mass fraction of saturated hydrocarbon of the petroleum sample, computer program calculation module 390, e.g., to calculate aromatic ring number families of the petroleum sample, and computer program calculation module 395, e.g., to calculate carbon number. Data storage memory 480 stores results and other data generated by the one or more modules of the present invention.

It is to be understood that the computer system 400 can be any computer such as a personal computer, minicomputer, workstation, mainframe, a dedicated controller such as a programmable logic controller, or a combination thereof. While the computer system 400 is shown, for illustrative purposes, as a single computer unit, the system can comprise a group of computers which can be scaled depending on the processing load and database size.

Computer system 400 preferably supports an operating system, for example stored in program storage memory 470 and executed by the processor 420 from volatile memory. According to an embodiment of the invention, the operating system contains instructions for interfacing computer system 400 to the Internet and/or to private networks.

The system and method of the present invention have been described above and with reference to the attached figures; however, modifications will be apparent to those of ordinary skill in the art and the scope of protection for the invention is to be defined by the claims that follow.

We claim:

1. A method for evaluating a hydrocarbon oil sample and calculating a mass fraction of sulfur compounds and aromatic hydrocarbon compounds of the hydrocarbon oil sample, the method comprising:
    providing a computer system that includes a processor coupled to non-volatile memory, determining total sulfur content of the hydrocarbon oil sample, and entering into the non-volatile memory the total sulfur content of the hydrocarbon oil sample,
    analyzing the hydrocarbon oil sample, subjected to solvent preparation, with a time-of-flight (TOF) mass spectrometer (MS) equipped with atmospheric pressure photo ionization (APPI) to obtain APPI TOF mass spectrometric data, entering the APPI TOF mass spectrometric data into the non-volatile memory, using the processor to calculate a molecular weight distribution and entering into the non-volatile memory the molecular weight distribution of the hydrocarbon oil sample;
    analyzing the hydrocarbon oil sample with a Fourier transform ion cyclotron resonance (FT-ICR) mass spectrometer equipped with APPI, in which parameters on the FT-ICR mass spectrometer are tuned to reproduce the molecular weight distribution obtained in the analysis of the hydrocarbon oil sample with the TOF MS to obtain FT ICR mass spectrometric data, entering the FT-ICR mass spectrometric data into the non-volatile memory, using the processor to calculate a determination of elemental formulas and enter into the non-volatile memory the determination of elemental formulas of the hydrocarbon oil sample;
    using the processor to calculate a mass fraction of sulfur compounds from the total sulfur content and the elemental formulas determination and enter into the non-volatile memory the mass fraction of sulfur compounds; and
    using the processor to calculate a mass fraction of aromatic hydrocarbon compounds from the mass fraction of sulfur compounds and from the elemental formula determination and entering into the non-volatile memory the mass fraction of aromatic hydrocarbon compounds.

2. The method of claim 1, further comprising:
    using the processor to calculate a mass fraction of saturated hydrocarbon compounds from the mass fraction of sulfur compounds and from the mass fraction of aromatic hydrocarbon compounds and entering into the non-volatile memory the mass fraction of saturated hydrocarbon compounds.

3. The method of claim 1, further comprising:
    using the processor to calculate an aromatic ring number families distribution from double-bond equivalent (DBE) values for each aromatic compound class and entering into the non-volatile memory the aromatic ring number families distribution,
    wherein the calculation is performed using the mass fraction of sulfur compounds, and using the mass fraction of aromatic hydrocarbon compounds.

4. The method of claim 1, further comprising:
    using the processor to calculate carbon number distributions for each aromatic ring number family and entering into the non-volatile memory the carbon number distributions for each aromatic ring number family,
    wherein the calculation is performed using the aromatic ring number families calculated from the DBE values for each compound class.

5. The method of claim 1, further comprising:
    analyzing the hydrocarbon oil sample with oxidative combustion followed by chemiluminescence detection to obtain chemiluminescence data, entering the chemiluminescence data into the non-volatile memory, and using the processor to calculate a total nitrogen content of the hydrocarbon oil sample based upon the chemiluminescence data and enter into the non-volatile memory the total nitrogen content of the hydrocarbon oil sample, and
    using the processor to calculate a mass fraction of nitrogen compounds from the total nitrogen determination and the elemental formulas determination and enter into the non-volatile memory the mass fraction of nitrogen compounds.

6. The method of claim 1, further comprising:
    using the processor to calculate a mass fraction of saturated hydrocarbon compounds from the mass fraction of sulfur compounds, from the mass fraction of nitrogen compounds, and from the mass fraction of aromatic hydrocarbon compounds and enter into the non-volatile memory the mass fraction of saturated hydrocarbon compounds.

7. The method of claim 5, further comprising:
    using the processor to calculate aromatic ring families distribution from double-bond equivalent (DBE) values for each aromatic compound class, wherein the calculation is performed using the mass fraction of sulfur compounds, the mass fraction of nitrogen compounds, and the mass fraction of aromatic hydrocarbon compounds and enter into the non-volatile memory aromatic ring families distribution.

8. The method of claim 7, further comprising:
    using the processor to calculate a carbon numbers distribution for each aromatic ring family and enter into the non-volatile memory carbon number distributions for each aromatic ring family,
    wherein the calculation is performed from the aromatic ring families calculated from the DBE values for each compound class.

9. The method of claim 7, further comprising:
using the processor to calculate a total alkyl chain length distribution for each aromatic ring family and enter into the non-volatile memory total alkyl chain length distributions for each aromatic ring family,
wherein the calculation is performed from the aromatic ring families calculated from the DBE values for each compound class.

10. A system for evaluating a hydrocarbon oil sample and calculating a mass fraction of sulfur compounds and aromatic hydrocarbon compounds of the hydrocarbon oil sample, the system comprising:
a non-volatile memory device that stores calculation modules and data;
a processor coupled to the non-volatile memory;
an X-ray fluorescence (XRF) spectrometer that analyzes the hydrocarbon oil sample to derive XRF spectrometric data, which is stored in the non-volatile memory;
a total nitrogen analyzer using oxidative combustion followed by chemiluminescence detection that analyzes the hydrocarbon oil sample to derive chemiluminescence spectrometric data, which is stored in the non-volatile memory;
a time-of-flight (TOF) mass spectrometer equipped with atmospheric pressure photo ionization (APPI), that analyzes the hydrocarbon oil sample to derive TOF mass spectrometric data, which is stored in the non-volatile memory;
a Fourier transform ion cyclotron resonance (FT-ICR) mass spectrometer equipped with APPI, that analyzes the hydrocarbon oil sample to derive FT-ICR mass spectrometric data, in which parameters of the FT-ICR mass spectrometer are tuned to reproduce the molecular weight distribution obtained from the TOF mass spectrometric data, and wherein the derived FT-ICR mass spectrometric data is stored in the non-volatile memory;
a first calculation module that, when executed by the processor, calculates a total sulfur content of the hydrocarbon oil sample based upon the XRF spectrometric data, and enters the calculated total sulfur content into the non-volatile memory;
a second calculation module that, when executed by the processor, calculates a molecular weight determination of the hydrocarbon oil sample from the TOF mass spectrometric data, and enters the calculated molecular weight distribution into the non-volatile memory;
a third calculation module that, when executed by the processor, produces a determination of elemental formulas of the hydrocarbon oil sample from the FT-ICR mass spectrometric data, and enters the calculated determination of elemental formulas into the non-volatile memory; and
a fourth calculation module that, when executed by the processor, determines a mass fraction of sulfur compounds from the total sulfur content and the determination of elemental formulas, and enters the calculated mass fraction of sulfur compounds into the non-volatile memory;
a fifth calculation module that, when executed by the processor, determines a mass fraction of nitrogen compounds from the total nitrogen content and the determination of elemental formulas, and enters the calculated mass fraction of nitrogen compounds into the non-volatile memory; and
a sixth calculation module that, when executed by the processor, calculates and enters into the non-volatile memory the mass fraction of aromatic hydrocarbon compounds from the mass fraction of sulfur compounds, and from the elemental formulas determination.

11. The system of claim 10, further comprising:
a seventh calculation module that, when executed by the processor, calculates and enters into the non-volatile memory a mass fraction of saturated hydrocarbon compounds from the mass fraction of sulfur compounds, from the mass fraction of nitrogen compounds, and from the mass fraction of aromatic hydrocarbon compounds.

12. The system of claim 10, further comprising:
a eighth calculation module that, when executed by the processor, calculates and enters into the non-volatile memory aromatic ring number families from double-bond equivalent (DBE) values for each aromatic compound class, wherein the calculation is performed using the mass fraction of sulfur compounds, using the mass fraction of nitrogen compounds, and using the mass fraction of aromatic hydrocarbon compounds.

13. The system of claim 12, further comprising:
a ninth calculation module that, when executed by the processor, calculates and enters into the non-volatile memory carbon numbers for each aromatic ring family, wherein the calculation is performed using the aromatic ring number families calculated from the DBE values for each compound class.

* * * * *